United States Patent
Sharrock et al.

(10) Patent No.: US 7,616,315 B2
(45) Date of Patent: Nov. 10, 2009

(54) ASSAY DEVICES AND METHODS

(75) Inventors: Stephen P. Sharrock, Bedford (GB);
Andrew P. Phelan, Bedford (GB)

(73) Assignee: Inverness Medical Switzerland GmbH, Zug (CH)

( * ) Notice: Subject to any disclaimer, the term of this patent is extended or adjusted under 35 U.S.C. 154(b) by 195 days.

(21) Appl. No.: 11/773,325

(22) Filed: Jul. 3, 2007

(65) Prior Publication Data

US 2008/0213875 A1    Sep. 4, 2008

Related U.S. Application Data

(63) Continuation of application No. 10/741,416, filed on Dec. 19, 2003, now Pat. No. 7,239,394, and a continuation of application No. 10/742,459, filed on Dec. 19, 2003, now Pat. No. 7,317,532, and a continuation of application No. 10/816,216, filed on Apr. 1, 2004, now Pat. No. 7,315,378.

(60) Provisional application No. 60/508,001, filed on Oct. 2, 2003.

(30) Foreign Application Priority Data

| Jun. 4, 2003 | (GB) | ................................ 0312801.4 |
| Jun. 4, 2003 | (GB) | ................................ 0312802.2 |
| Jun. 4, 2003 | (GB) | ................................ 0312815.4 |

(51) Int. Cl.
*G01N 21/00* (2006.01)

(52) U.S. Cl. .................................................. 356/436

(58) Field of Classification Search .................. 356/39, 356/436; 204/403.01, 403.03
See application file for complete search history.

(56) References Cited

U.S. PATENT DOCUMENTS

| 3,941,477 A | 3/1976 | Schodl et al. |
| 4,399,362 A | 8/1983 | Cormier et al. |
| 4,420,566 A | 12/1983 | Jessop et al. |
| 4,523,853 A | 6/1985 | Rosenbladt et al. |
| 4,676,653 A | 6/1987 | Strohmeier et al. |
| 4,995,402 A | 2/1991 | Smith et al. |
| 5,049,487 A | 9/1991 | Phillips et al. |
| 5,114,350 A | 5/1992 | Hewett |
| 5,304,468 A | 4/1994 | Phillips et al. |
| 5,344,754 A | 9/1994 | Zweig |
| 5,504,013 A | 4/1996 | Senior |
| 5,580,794 A | 12/1996 | Allen |
| 5,679,584 A | 10/1997 | Mileaf et al. |
| 5,786,220 A | 7/1998 | Pronovost et al. |

(Continued)

FOREIGN PATENT DOCUMENTS

DE    196 28 562    1/1998

(Continued)

OTHER PUBLICATIONS

Search Report dated Dec. 1, 2003 for GB 0312815.4.

(Continued)

*Primary Examiner*—Kara E Geisel
(74) *Attorney, Agent, or Firm*—Foley Hoag LLP

(57) ABSTRACT

A device for determining an assay result may include a test strip, a light source system, a light detection system, and a processor.

1 Claim, 14 Drawing Sheets

U.S. PATENT DOCUMENTS

| | | | |
|---|---|---|---|
| 5,837,546 | A | 11/1998 | Allen et al. |
| 5,885,839 | A | 3/1999 | Lingane et al. |
| 5,889,585 | A | 3/1999 | Markart et al. |
| 5,968,835 | A | 10/1999 | Aoki et al. |
| 5,968,839 | A | 10/1999 | Blatt et al. |
| 6,055,060 | A | 4/2000 | Bolduan et al. |
| 6,156,271 | A | 12/2000 | May |
| 6,194,222 | B1 | 2/2001 | Buechler et al. |
| 6,235,241 | B1 | 5/2001 | Catt et al. |
| 6,361,956 | B1 | 3/2002 | Hanninen et al. |
| 6,399,398 | B1 | 6/2002 | Cunningham et al. |
| 6,448,067 | B1 | 9/2002 | Tajnafoi et al. |
| 6,707,554 | B1 | 3/2004 | Miltner et al. |
| 6,825,918 | B2 | 11/2004 | Eisenmann et al. |
| 6,847,451 | B2 * | 1/2005 | Pugh ................... 356/436 |
| 6,951,631 | B1 | 10/2005 | Catt et al. |
| 7,018,847 | B2 | 3/2006 | Mendel-Hartvig et al. |
| 7,154,593 | B2 * | 12/2006 | Eisenmann et al. ........... 356/39 |
| 2002/0192833 | A1 | 12/2002 | Pan et al. |
| 2003/0180815 | A1 | 9/2003 | Rawson et al. |
| 2004/0152208 | A1 | 8/2004 | Hutchinson |
| 2004/0152209 | A1 | 8/2004 | Zin et al. |

FOREIGN PATENT DOCUMENTS

| | | |
|---|---|---|
| EP | 0 291 194 B1 | 11/1988 |
| EP | 0 362 809 | 4/1990 |
| EP | 0 653 625 | 5/1995 |
| EP | 0 728 309 B1 | 8/1997 |
| EP | 0 819 943 A2 | 1/1998 |
| EP | 0 826 777 | 3/1998 |
| EP | 0 833 145 | 4/1998 |
| EP | 0 782 707 B1 | 11/1998 |
| EP | 1 046 122 | 10/2000 |
| EP | 0 291 194 B2 | 7/2003 |
| EP | 0 291 194 B8 | 10/2003 |
| GB | 2365526 | 2/2002 |
| WO | WO-94/04925 | 3/1994 |
| WO | WO-98/25143 | 6/1998 |
| WO | WO-99/35602 | 7/1999 |
| WO | WO-00/19185 | 4/2000 |
| WO | WO-2004/070353 | 8/2004 |

OTHER PUBLICATIONS

Search Report dated Jul. 3, 2006 for FR 0406067.
European Search Report dated Jul. 3, 2006 for EP 04 25 3076.

* cited by examiner

ASSAY DEVICES AND METHODS

CROSS-REFERENCE TO RELATED APPLICATIONS

This application is a continuation of U.S. application Ser. No. 10/741,416, filed Dec. 19, 2003, now U.S. Pat. No. 7,239,394, which claims the benefit of GB application Ser. No. 0312815.4, filed Jun. 4, 2003, and is also a continuation of U.S. application Ser. No. 10/742,459, filed Dec. 19, 2003, which claims the benefit of GB application Ser. No. 0312801.4, filed Jun. 4, 2003, and is also a continuation of U.S. application Ser. No. 10/816,216, filed Apr. 1, 2004, which claims the benefit of GB application Ser. No. 0312802.2, filed Jun. 4, 2003. Each of the aforementioned U.S. applications claims the benefit of U.S. Provisional Patent Application Ser. No. 60/508,001, filed Oct. 2, 2003. Each of the aforementioned U.S. and GB applications is hereby incorporated herein by this reference.

DETAILED DESCRIPTION

Figure 1:
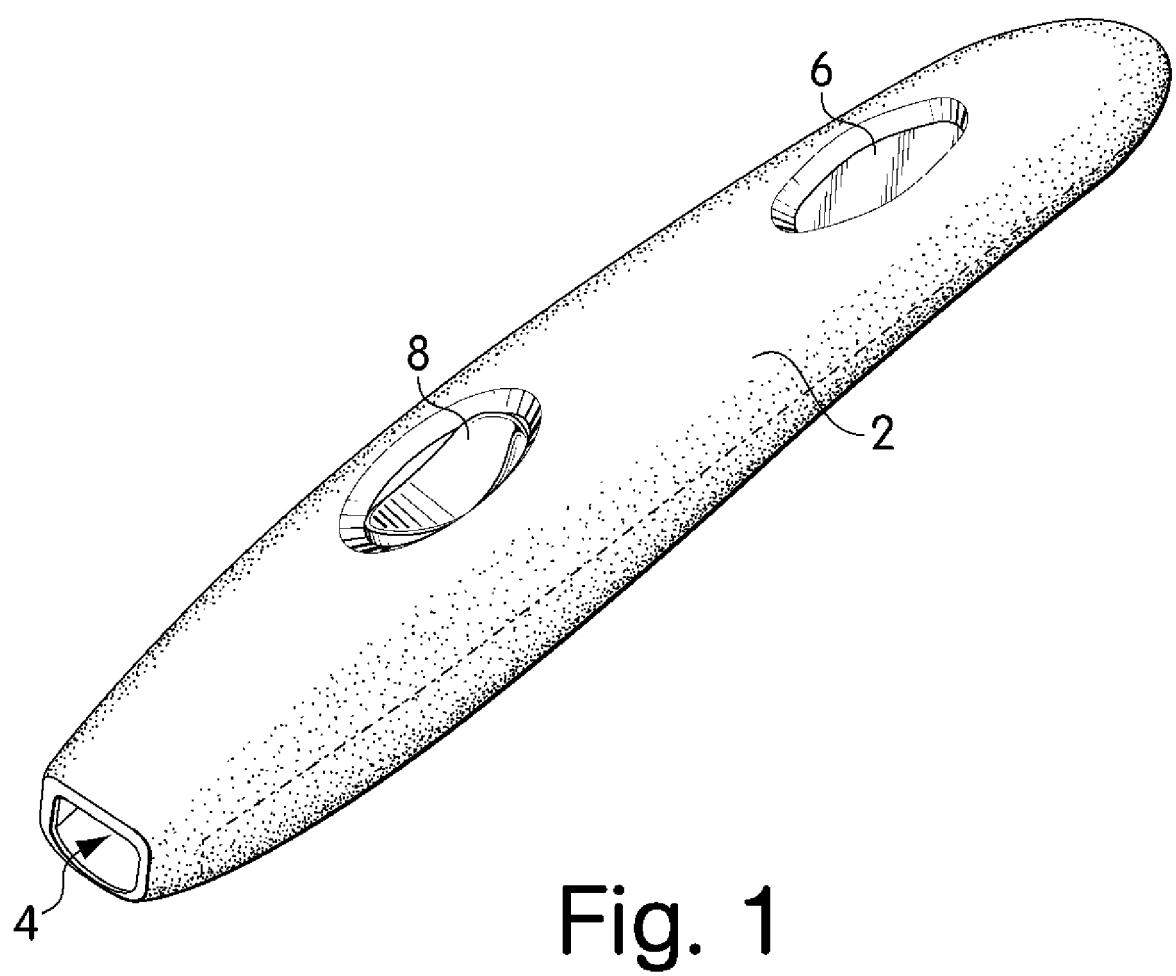
FIG. 1 is a perspective view of one embodiment of an assay result reading device in accordance with the present disclosure.

The present disclosure concerns, among other things, assay devices for use with test strips.

For the avoidance of doubt, it is expressly stated that any of the features described herein as "preferred", "desirable", "convenient", "advantageous" or the like may be adopted in an embodiment in combination with any other feature or features so-described, or may be adopted in isolation, unless the context dictates otherwise.

1. Early Determination of Assay Results

It is preferred, but by no means essential, that the assay is a lateral flow type assay, in which a liquid sample, possibly comprising the analyte of interest, is applied to a liquid transport means (typically comprising a porous carrier, such as nitrocellulose) and migrates therealong. Assays of this type are well known to those skilled in the art and are disclosed, for example, in EP0291194.

The signal which accumulates during performance of the assay may be anything suitable for the purpose. Conveniently the signal accumulation comprises formation or accumulation of a readily detectable substance (e.g. a coloured reaction product). More especially the assay preferably comprises accumulation of a labelled reagent, typically deposition or accumulation of the labelled reagent in the test zone or detection zone of a lateral flow assay stick. The label may be, for instance, an enzyme, a radiolabel, a fluorochrome, a coloured particle or the like. In particular the assay conveniently involves the accumulation of a specific binding reagent in the detection zone of a lateral flow assay stick, the specific binding reagent being labelled with a particle of gold or a coloured polymer, such as latex.

Generally speaking, presence of the analyte of interest in the sample will tend to cause accumulation of signal. However, in other formats (especially for example, competition or displacement formats), it is the absence of the analyte of interest which may cause the accumulation of the relevant signal.

Again, generally speaking, in those embodiments of the device and method of the present disclosure where presence of the analyte of interest leads to accumulation of the signal, the upper threshold value is set such that signal levels below this value are regarded as negative (i.e. the analyte is not present) and levels above are regarded as positive.

If after a certain period of time, the rate or amount of signal accumulation has not reached the lower threshold limit, it is considered that the signal will never reach the upper threshold even if the reaction were allowed to proceed to completion, and an early negative result is then displayed. This would represent the case of a fluid sample having a very low analyte concentration.

Conversely, a result can be promptly displayed if the rate or amount of signal accumulation crosses the upper threshold limit. In the case of a high analyte concentration, the reading will cross the upper threshold limit at an earlier time and therefore an earlier than usual result may be displayed.

In the intermediate case wherein the rate or amount of signal accumulation crosses the lower threshold limit before a certain period of time has elapsed but does not exceed the upper threshold, the reader will wait until the reading crosses the upper threshold before displaying a positive result. If the reading does not pass the upper threshold before a further second period of time has elapsed, a negative result is displayed.

Thus the device is able to display the results as soon as conveniently possible rather than necessarily wait for a preset time to elapse. A device in accordance with the present disclosure can therefore generally indicate an assay result more quickly, especially where the analyte concentration is very high or very low.

The reaction which leads to signal accumulation may be any suitable reaction e.g. a conventional chemical reaction between two chemical entities, or an enzyme-catalysed reaction or reaction requiring some other catalyst, or may be a binding reaction. Preferred binding reactions will involve the binding of at least one biological molecule. More especially, the reaction will preferably involve the binding of members of a specific binding pair ("sbp"). Sbps are well known to those skilled in the art and include, inter alia, enzyme/substrate, antibody/antigen, and ligand/receptor pairs.

A preferred reaction involves the binding of a labelled analyte/reagent complex to specific binding reagent immobilised in a detection zone of a lateral flow assay stick, the signal being accumulation of the label in the detection zone.

The assay result reader will typically comprise an optical detection system to detect accumulation of the label. Conveniently the reader device will comprise means of generating a signal (typically a digital signal) which is proportional to the amount of label accumulated. Desirably the optical detection system may measure an optical property, such as the amount of light reflected and/or transmitted from a detection zone in which the label accumulates. Suitable optical systems are known to those skilled in the art and are disclosed, for example, in EP 0653625.

The preferred optical detection system will comprise at least one light source and at least one photodetector (such as a photodiode). Preferred light sources are light emitting diodes or LED's. Reflected light and/or transmitted light may be measured by the photodetector. For the purposes of this disclosure, reflected light is taken to mean that light from the light source is reflected from the porous carrier or other liquid transport means onto the photodetector. In this situation, the detector is typically provided on the same side of the carrier as the light source. Transmitted light refers to light that passes through the carrier and typically the detector is provided on the opposite side of the carrier to the light source. For the purposes of a reflectance measurement, the carrier may be provided with a backing such as a white reflective MYLAR® plastic layer. Thus light from the light source will fall upon the carrier, some will be reflected from its surface and some will penetrate into the carrier and be reflected at any depth up to and including the depth at which the reflective layer is provided. Thus, a reflectance type of measurement may actually involve transmission of light through at least some of the thickness of the porous carrier.

In a preferred embodiment the assay result reading device comprises a housing formed from a light-impermeable material, conveniently a synthetic plastics material such as polycarbonate, ABS, polystyrene, high density polyethylene, or polypropylene or polystyrol containing a suitable light-blocking pigment.

The housing of the assay result reader typically comprises an aperture such that a test strip may be releasably inserted into and (preferably) engaged with the housing. The housing is designed such that ambient light entering the interior of the reader is kept to an absolute minimum. Desirably suitable alignment and fixing means are provided within the housing such that the test strip remains in a fixed position when inserted. The light sources are arranged in the housing such that, when the test strip has been correctly inserted, they are correctly aligned with the respective zone to be measured.

The assay test strip may be any conventional lateral flow assay test strip such as those disclosed in EP291194 or U.S. Pat. No. 6,352,862. The test strip preferably comprises a porous carrier containing a particulate labelled specific binding reagent and an unlabelled specific binding reagent. The light sources and corresponding photodetectors are preferably so aligned such that during use, light from the light sources falls upon the respective zones on the porous carrier and is reflected or transmitted to the respective photodetectors. The photodetectors generate a current proportional to the amount of light falling upon it which is then fed through a resistor to generate a voltage. The amount of light reaching the photodetector depends upon the amount of coloured particulate label present and therefore the amount of analyte. Thus the amount of analyte present in the sample may be determined. This method of optically determining the analyte concentration is described more fully in EP653625.

In a typical embodiment, the assay result reading device will comprise one or more of the following: a central processing unit (CPU) or microcontroller; one or more LED's; one or more photodetectors; a power source; and associated electrical circuitry. The power source may be a battery or any other suitable power source (e.g. a photovoltaic cell).

Conveniently the CPU or microcontroller will be programmed so as determine, from the output of the photodetectors, the rate or amount of signal accumulation and to compare this with the upper and lower threshold values.

In order to declare the assay result the reader will generally possess some manner of indicating or communicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether or not the result of the particular assay should be disregarded e.g. because a control result has failed. If the reading device determines that a particular assay result should be disregarded it may prompt the user to repeat the assay. Displays suitable for displaying this sort of information are known to those skilled in the art and disclosed, for example, in WO 99/51989.

Advantageously the reader device will have some means of determining elapsed time, such as an integral clock device.

Preferably the reading device is activated when an assay device is inserted into the reader device. This may be achieved by the user pressing a switch or button but, more preferably, is effected automatically, such that insertion of an assay device in the correct orientation and into the correct position within the reader causes activation thereof. To facilitate this, it is preferred that the reader and the assay device are shaped and dimensioned so as to provide a precise three dimensional fit. This concept is disclosed and described in EP 0833145. In particular activation of the reader and/or insertion of an assay device into the reader may trigger the reader to commence timing.

Desirably the reader is so programmed as to make a first determination of the rate or amount of signal accumulation after a predetermined time interval. (Say, for example, 10 seconds after activation). If the rate or amount of signal accumulation exceeds the upper threshold or is below the lower threshold, and the control values (if any) are within acceptable limits, the assay can be safely terminated and the results (positive, negative, or a semi-quantitative result) indicated to the user. If however the determined rate or amount of signal accumulation is above the lower threshold but below the upper threshold, the assay must be continued. The signal in this instance may be said to be an intermediate signal.

Typically there is an end-point, $t_e$, at which the reader device considers the assay complete. If the signal is still below the upper threshold value at $t_e$ the result of the assay is negative (in those formats in which it is the presence of the analyte of interest which leads to formation of the signal). The end-point of the assay may not necessarily be at completion of the reaction. Indeed, the end-point $t_e$ will normally be considered to have been reached before the reaction is complete.

The $t_e$ end point may conveniently be determined by the reader by reference to a particular time point (i.e. $t_e$ may be considered to occur a particular amount of time after commencement of the assay e.g. a particular interval after activation of the reader and/or insertion of an assay stick into the reader and/or application of the sample to the test stick). For the purposes of illustration, $t_e$ will typically occur between 1 and 10 minutes, preferably between 1 and 5 minutes after commencement of the assay.

Desirably the assay result reader will be programmed so as to repeat the test measurement if an intermediate signal is obtained. In a simple embodiment the measurement is repeated at $t_e$. Preferably however the measurement is repeated one or more times before the end point. Most preferably the reader device is programmed to repeat the measurement at regular intervals (say, for instance 1 second or 5 second intervals) until the signal exceeds the upper threshold or until $t_e$, which ever occurs first.

Inclusion of a clock or other timing device in the assay result reader is desirable so that the reader can automatically take measurements at predetermined time points without further user input.

Thus, for example, the reader may be programmed to take measurements at an initial time point $t_o$ and, if necessary to make repeated measurements at any desired interval thereafter until the signal exceeds the upper threshold or $t_e$ is reached, as described above.

In addition, a clock or other timing device facilitates the reading device in determining the rate of signal accumulation. If measurements of the amount of signal are taken at two or more time points (with a known temporal separation), then the rate of signal accumulation may readily be calculated.

It should be noted that the rate or amount of signal accumulation could be measured either in absolute terms or as a relative valve (e.g. compared to a control or other comparison value, optionally obtained from a substantially contemporaneous reaction).

2. Optical Arrangements

The optical arrangements for assay readers described herein promote simplicity and economy. The manufacturing cost of the device is an especially important consideration if the reader is intended to be disposable; the photodetectors themselves, being relatively expensive components, form a significant part of the overall cost.

A further advantage is that the arrangement can provide greater accuracy and reduce the need for accurate positioning of the test strip relative to the reader. Suppose, for example, a test strip were provided with two separate, but closely spaced, control zones and a photodetector were positioned in the reader so as to be between the two control zones. If the test strip were slightly misaligned, laterally, relative to the assay reader device, the signal from one of the control zones would be less intense as the zone in question would be further from the photodetector. However, the other control zone would necessarily be closer to the photodetector by a corresponding amount, and would therefore provide a stronger signal to compensate for the weaker signal from the other zone. Furthermore it has been observed that the amount of bound material present at a particular zone will vary along the length of the zone in the direction of liquid flow. Preferential binding of the analyte takes place at the leading boundary edge and diminishes along the length of the zone in the direction of liquid flow. Thus any misalignment may result in a greater error than might have been expected if the analyte were captured in a uniform fashion. U.S. Pat. No. 5,968,839 discloses an electronic assay reader for use with a test strip, wherein it is attempted to compensate for this non-uniform binding by the provision in the relevant binding zone of a plurality of deposits of immobilised capture reagent, the density of which deposits increases from the leading boundary to the trailing edge of the zone.

Similarly, some of the arrangements described herein also reduce the requirement for precise relative positioning of the test strip and the assay result reading device: there is an in-built signal compensation for any misalignment between the test strip and the assay result reader for any zone which is commonly read by the two or more photodetectors, because relative movement of the commonly read zone away from one of the photodetectors will necessarily (within certain limits) involve movement by a corresponding amount towards the other photodetector/s.

The light emanating from the zone or zones, as appropriate, may be light which is reflected from the test strip or, in the case of a test strip which is transparent or translucent (especially when wet e.g. following the application of a liquid sample), light which is transmitted through the test strip. For the purposes of the present specification, light incident upon a particular zone of a test strip from a light source, and reflected by the strip or transmitted therethrough, may be regarded as "emanating" from the strip, although of course the light actually originates from the light source.

The preferred light sources are light emitting diodes (LED's), and the preferred photodetector is a photodiode.

Reflected light and/or transmitted light may be measured by the photodetector. For the present purposes, reflected light is taken to mean that light from the light source is reflected from the test strip onto the photodetector. In this situation, the detector is typically provided on the same side of the test strip as the light source. Transmitted light refers to light that passes through the test strip and typically the detector is provided on the opposite side of the test strip to the light source. For the purposes of a reflectance measurement, the test strip may be provided with a backing such as a white reflective MYLAR® plastic layer. Thus light from the light source will fall upon the test strip, some will be reflected from its surface and some will penetrate into the test strip and be reflected at any depth up to and including the depth at which the reflective layer is provided. Thus, a reflectance type of measurement may actually involve transmission of light through at least some of the thickness of the test strip. Generally, measurement of reflected light is preferred.

It is especially preferred that the reading device of the second aspect comprises a plurality of light sources, each light source being incident upon a respective zone of the test strip.

In principle, an assay result reading device in accordance with the present disclosure may comprise any number of light sources and any number of photodetectors. For example, one embodiment includes three light sources, each illuminating a respective zone of a test strip, and a single photodetector which is shared by all three zones. In practice it is difficult to arrange for more than three zones to share a single photodetector, because the photodetector will have trouble in detecting a sufficiently strong signal from those zones which are furthest away.

In preferred embodiments, an assay result reader feature both "shared" photodetectors as well as "commonly read" zones; i.e., a single photodetector can receive light emanating from more than one zone, and light emanating from a single zone is received by more than one photodetector. In this instance, the reader will typically include a plurality of light sources and a smaller plurality of photodetectors. In particular, where the reader comprises x light sources for illuminating the test strip, it will comprise x−1 photodetectors. The number of detectors required might be reduced still further by sharing of the photodetectors between the respective light sources, e.g. using three photodetectors to detect light emanating from an assay test strip that has been illuminated by five light sources.

More specifically, a preferred embodiment of an assay result readers includes first, second and third light sources, each light source illuminating respective first, second or third zones of a test strip. Conveniently the first light source illuminates a test zone or detection zone; the second light source illuminates a reference zone; and the third light source illuminates a control zone. The test or detection zone is a zone of the test strip in which an optical signal is formed (e.g. accumulation or deposition of a label, such as a particulate coloured binding reagent) in the presence or absence, as appropriate, of the analyte of interest. (By way of explanation some assay formats, such as displacement assays, may lead to the formation of signal in the absence of the analyte of interest). The control zone is a zone of the test strip in which an optical signal is formed irrespective of the presence or absence of the analyte of interest to show that the test has been correctly performed and/or that the binding reagents are functional. The reference zone is a zone wherein, typically, only "background" signal is formed which can be used, for example, to calibrate the assay result reading device and/or to provide a background signal against which the test signal may be referenced.

In this particular preferred embodiment, the reader also includes two photodetectors. The first photodetector is substantially adjacent to or primarily associated with the first light source and is intended to detect light emanating the zone of the test strip illuminated by the respective light source. However, the photodetector is so positioned as to be also capable of detecting some of the light emanating from the second zone of the test strip, illuminated by the second light source.

The second photodetector is substantially adjacent to or primarily associated with the third light source and is intended to detect light emanating from the zone of the test strip illuminated by the respective light source. However the photodetector is so positioned as to be also capable of detecting some of the light emanating from the second zone of the test strip, illuminated by the second light source.

Accordingly, this embodiment features a "shared" photodetector, because it includes a plurality of light sources and a photodetector which detects light emanating from at least two spatially separated zones of the test strip. In addition, this embodiment has "commonly read" zones, because it comprises two photodetectors, both of which are able to detect some of the light emanating from a zone of the test strip (in this instance, two photodetectors are able to detect light emanating from the second zone of the test strip).

It is preferred that, when the assay strip is correctly inserted into a reader device, a commonly read zone will be at a position intermediate between the two photodetectors, such that (within certain limits) a lateral movement away from one of the photodetectors will inevitably involve a corresponding lateral movement towards the other photodetectors, so as to allow for the desired signal compensation effect. Typically, but not essentially, the commonly read zone will be approximately equidistant from the two photodetectors when the test strip is correctly positioned within the reader.

It is also preferred that, where an assay result reading device includes a plurality of light sources, these are advantageously arranged such that a particular zone is illuminated only by a single one of the plurality of light sources. For example, optical baffles may be provided between or around the light sources so as to limit the portion of the test strip illuminated by each light source.

3. Flow Rate Sensing

In describing the various embodiments, "fluid sample" refers to any liquid material suspected of containing the analyte of interest. Such samples may include human, animal or man-made samples. Typically, the sample is an aqueous solution or biological fluid.

Examples of biological fluids include urine, blood, serum, plasma, saliva, interstitial fluid and so on. Other samples which can be used include water, food products, soil extracts and the like for the performance of industrial, environmental, or food production assays as well as medical diagnostic assays. In addition, a solid material suspected of containing the analyte can be used as the test sample once it is modified to form a liquid medium which may include further treatment in order to release the analyte.

Any suitable analyte or analytes of interest may be measured. Analytes that are particularly of interest include proteins, haptens, immunoglobulins, hormones, polynucleotides, steroids, drugs, infectious disease agents (e.g. of bacterial or viral origin) such as *Streptococcus*, *Neisseria* and *Chlamydia*, drugs of abuse, and biological markers such as cardiac markers and so on.

Typically the disclosed assay result reading devices and methods are adapted to perform a diagnostic assay i.e. to provide information about the health status of a mammalian (typically a human) individual subject.

It is preferred to calculate the rate of progress of the liquid sample (rather than the extent thereof) along the liquid transport carrier.

Conveniently the flow rate is calculated between two zones on the liquid transport carrier, such that the presence of the liquid sample at, or passage thereof through, a first, upstream zone is detected, and likewise the present of the liquid sample at, or passage through, a second, downstream zone is detected. If the distance between the two zones is fixed and/or known, the relative or absolute flow rate of the liquid sample can be readily calculated by measuring the amount of time which elapses between detection of the liquid sample at the first and second zones.

In principle, the first and second zones may be anywhere on the liquid transport carrier so, for example, the first zone could be at the extreme upstream end and the second zone could at the extreme downstream end. The distance between the two zones (and therefore the time travel of fluid sample) may be chosen to be any that is convenient and is likely to depend upon the nature of the analyte to be determined and the physical dimensions and characteristics of the liquid transport carrier. For example the liquid transport carrier may comprise one or more microfluidic channels optionally containing one or more various microfluidic elements such as a red-blood cell separation means, time-gates, or fluid rate controlling means, all of which will influence the rate of travel of sample. In practice, it is desirable that the two zones are at a separation such that, at normal flow rates, a sufficiently accurate flow rate may be calculated within the time frame of the assay, so as not to delay the assay process or assay result determination. For an assay for the detection and/or quantification of the pregnancy hormone hCG, for example, a desirable time would be between 5 and 60 seconds.

Advantageously the presence of the liquid sample at, or passage through, one or more additional zones on the liquid transport carrier is detected. This allows for a more accurate calculation of the flow rate. A larger number of flow rate calculation zones may be advantageous when the acceptable range of flow rates is rather narrow, or where the flow rate may vary at different portions of the liquid transport carrier (e.g. where there are portions with different flow characteristics, for instance, due to the incorporation of microfluidic elements).

In addition the provision of a plurality of "check zones" allows for checking that the liquid sample progresses through each of the zones in the expected sequence, thereby alerting the user to an abnormal flow pattern if the liquid sample is detected at a downstream zone in advance of detection at a particular upstream zone. Such abnormal flow patterns can occur for instance when a porous carrier is flooded by liquid samples ("oversampling").

If the calculated flow rate is outside of the predetermined acceptable limits, then the result of the assay may be declared invalid. Thus the flow rate calculation can act as a control feature. If the calculated flow rate is too high, due to flooding of the porous carrier (e.g. as a result of oversampling; or a result of a faulty assay device due to defects in manufacture, or damage in storage or in use) the user can be alerted and the assay result disregarded. Equally, if the calculated flow rate is too low (e.g. due to undersampling) the assay result can be disregarded. Thus, errors due to, for example, over- or under-sampling, may be avoided.

In principle any property of the liquid sample could be measured in order to calculate the rate and/or extent of progress of the liquid, such as its electrical capacitance, conductivity or resistivity. The porous carrier or other liquid transport carrier may comprise a substance which undergoes a detectable change in the presence of the liquid sample. For example nitrocellulose, commonly used as a porous carrier in lateral flow assay strips, is opaque (or substantially so) when dry, but its opacity is significantly reduced upon wetting. Thus measurement or detection of the change in optical reflectance or transmissivity of a nitrocellulose carrier upon wetting by a liquid sample may be sufficient to detect the rate and/or extent of progress of the liquid sample.

Preferably the means for calculating the rate and/or extent of the progress of the liquid sample applied to the liquid transport carrier comprises an optical detection system. Such an optical detection system will typically generate one or more signals (advantageously, electrical signals) in a manner responsive to the rate and/or extent of the progress of the liquid sample. In a preferred embodiment, a suitable optical system comprises at least two light sources and at least one photodetector, or conversely at least one light source and at least two photodetectors, so as to be able to make optical measurements at least two spatially separated zones of the liquid transport carrier.

In principle the light source could be external to the assay result reader e.g. ambient light. However, this is extremely likely to introduce variation, and it is therefore greatly preferred that: (a) the assay result reading device is provided with at least one integral light source (LED's are found especially convenient in this regard); and (b) the assay result reading device is provided with a housing or casing which substantially excludes, or at least greatly restricts, ambient light from entering the interior of the reading device. For present purposes, a housing or casing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the interior space within the housing: a test strip or similar porous carrier may be inserted through the aperture so as to perform an assay.

The liquid sample per se may have an optical property (e.g. colour) which renders it amenable to optical detection and/or monitoring of its progress along the liquid transport carrier. For example, a blood sample will absorb strongly in the range 400 nm to 600 nm, due to the presence of haemoglobin. Alternatively the liquid sample may be doped, prior to application to the liquid transport carrier, with a readily detectable substance (e.g. a dye, fluorochrome or the like) which will not interfere with the performance of the assay but will facilitate detection (especially optical detection) of the rate and/or extent of the progress of the liquid sample.

In yet another arrangement, the liquid transport carrier is provided with a readily detectable substance which is transported by the liquid sample. Again, a dye, fluorochrome or the like may be suitable in this regard. The readily detectable substance may conveniently be releasably immobilised on a porous carrier or the like, so as to be released upon contact with the liquid sample. The readily detectable substance may be e.g. a coloured substance which does not interfere with the assay. In a preferred embodiment the readily detectable substance is a particulate label which is attached to a mobilizable specific binding reagent (having specific binding for the analyte), and detection of which label in a detection zone constitutes an essential feature of the assay.

The particulate label may be anything suitable for the purpose, including coloured latex, a dye sol, or particulate gold. Alternatively the particulate label may comprise a fluorophore which can be excited by an LED emitting radiation of a suitable wavelength.

The preferred optical detection system will comprise at least one light source and at least one photodetector (such as a photodiode). Preferred light sources are light emitting diodes or LED's. Reflected light and/or transmitted light may be measured by the photodetector. For the purposes of this disclosure, reflected light is taken to mean that light from the light source is reflected from the porous carrier or other liquid transport carrier onto the photodetector. In this situation, the detector is typically provided on the same side of the carrier as the light source. Transmitted light refers to light that passes through the carrier and typically the detector is provided on the opposite side of the carrier to the light source. For the purposes of a reflectance measurement, the carrier may be provided with a backing such as a white reflective MYLAR® plastic layer. Thus light from the light source will fall upon the carrier, some will be reflected from its surface and some will penetrate into the carrier and be reflected at any depth up to and including the depth at which the reflective layer is provided. Thus, a reflectance type of measurement may actually involve transmission of light through at least some of the thickness of the porous carrier.

In one embodiment the reader comprises a housing in which is contained at least two light sources (e.g. LED's) and respective photodetectors arranged to receive light from the LED's.

One of the light sources illuminates a first, upstream zone of the liquid transport carrier and another light source illuminates a second, downstream zone of the liquid transport carrier, and respective photodetectors are provided to detected light reflected and/or transmitted from the respective zones, the amount of such light which is reflected and/or transmitted depending on whether the liquid sample (optionally together with any light-absorbing or light-emitting substance transported thereby) has reached the zone(s) in question.

In a particularly preferred embodiment the assay result reading device comprises three light sources which illuminate respective first, second and third zones of the liquid transport carrier, and the flow rate of the liquid sample between at least two of the zones is measured.

Conveniently one of the zones from which measurements are made in the calculation of the flow rate is also a zone from which measurements are made in determining the result of the assay, for example, the first zone may be a zone in which analyte-specific labelled binding reagent is immobilised if analyte is present in the sample. Such a zone may be referred to as a test zone.

Desirably one of the zones from which measurements are made in the calculation of the flow rate is also a zone from which control measurements are made for the purpose of obtaining a control value, which is used to determine if the assay has been correctly performed. Such a zone may be referred to as a control zone.

It is advantageous that there is a zone, from which measurements are made in the calculation of the flow rate, which is also a zone from which measurements are made in calibration of the assay result reader. Such a zone may be referred to as a reference zone.

It is desirable that the components of the assay reader used in the detection and/or quantification of the analyte of interest are also used in calculating the flow rate of the liquid. This confers advantages of simplicity and economy, which are especially desirable for a disposable device. In particular, a preferred assay result reader has an optical detection system for detecting the presence and/or amount of the analyte of interest, and the same optical detection system is employed to make measurements for the purpose of calculating flow rates.

In a particularly preferred embodiment the assay result reader obtains measurements from a control zone, a reference zone and a test zone, the control zone being downstream from the reference zone which is itself downstream of the test zone (i.e. the reference zone is between the test and control zones). The reference zone allows for, inter alia, measurement of an optical property (e.g. reflectance and/or transmissivity) of the liquid transport carrier when wetted (e.g. a wetted porous carrier). Conveniently results obtained from the test and control zones are normalised relative to the reference zone, and this takes into account and compensates for any variation in the optical property of the sample. This is especially important when using biological samples, such as urine, which may vary widely in composition (e.g. concentration) and therefore vary in colour or colour intensity.

The housing of the assay result reader typically comprises an aperture such that a test strip may be releasably inserted into and (preferably) engaged with the housing. The housing is designed such that ambient light reaching the interior of the reading device is kept to an absolute minimum. Desirably suitable alignment and fixing means are provided within the housing such that the test strip remains in a fixed position when inserted. The light sources are arranged in the housing such that, when the test strip has been correctly inserted, the light sources are correctly aligned with the respective zones to be measured.

The assay test strip may be any conventional lateral flow assay test strip such as disclosed in EP291194 or U.S. Pat. No. 6,352,862. The test strip preferably comprises a porous carrier containing a particulate labelled specific binding reagent and an unlabelled specific binding reagent. The light sources and corresponding photodetectors are preferably so aligned such that during use, light from the light source or sources falls upon the respective zones on the porous carrier and is reflected or transmitted to the respective photodetectors. The photodetectors generate a current roughly proportional to the amount of light falling upon it which is then fed through a resistor to generate a voltage. The amount of light reaching the photodetector depends upon the amount of coloured particulate label present and therefore the amount of analyte. Thus the amount of analyte present in the sample may be determined. This method of optically determining the analyte concentration is described more fully in EP653625.

Alternatively, instead of using a test strip comprising a lateral flow porous carrier such as described by EP291194, a test strip having the binding reagents disposed within a capillary could be used, such as disclosed by U.S. Pat. No. 6,113,855.

In order to conduct an assay measurement using a assay result reading device in accordance with some of the preferred features, a test strip is inserted into the reader, and a liquid sample is then added to a sample receiving portion of the test strip. Alternatively a liquid sample may be applied to the test strip first, and the strip then inserted into the reader. The sample migrates along the porous carrier and reaches a first zone, typically the test zone. When sample is added to the strip, a coloured particulate label is resuspended and migrates along the carrier along with the fluid. As the fluid front of the sample reaches first zone, there is a reduction in light intensity reaching the photodetector since the coloured particulate label absorbs some of the light. This change in reflected or transmitted light intensity is recorded. In practice, a larger amount of the particulate label is present in the initial fluid front than in the subsequent fluid. In addition, if a binding reaction takes place in the test zone due to the presence of analyte, particulate label will tend to remain in the test zone. Thus the shape of the resultant voltage-time profile observed will depend upon whether the zone is a test, control or reference zone. For a three zone system, three voltage-time profiles will be recorded one for each zone, having a time lag due to the fact that measurement zones are spatially separated from one another and thus the time taken for the fluid front to reach the first zone is less than that taken to reach the second and so on.

From analysis of the voltage-time profiles for the respective zones and with knowledge of the distance between the zones, the rate of fluid flow may be determined. By use of a simple algorithm, the final assay reading may be rejected if the calculated flow rate has been determined to be too low or too high.

In a typical embodiment, the assay result reading device will typically further comprise one or more of the following: a central processing unit (CPU) or microcontroller; two or more LED's; two or more photodiodes; a power source; and associated electrical circuitry. The power source may comprise a battery or any other suitable power source (e.g. a photovoltaic cell). The CPU will typically be programmed so as to determine whether the calculated rate and/or extent of progress of the liquid sample is within predetermined limits.

Conveniently the assay result reading device will comprise some manner of indicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether the calculated rate and/or extent of progress of the liquid sample is within the predetermined acceptable limits, and thus whether or not the result of the particular assay should be disregarded. If the reading device determines that a particular assay result should be disregarded it may prompt the user to repeat the assay. Displays suitable for displaying this sort of information are known to those skilled in the art and disclosed, for example, in WO 99/51989.

EXAMPLES

Example 1

An embodiment of an assay result reading device having both "shared" photodetectors and "commonly read" zones is illustrated in FIG. 1.

The reading device is about 12 cm long and about 2 cm wide and is generally finger or cigar-shaped. In preferred embodiments, the housing is no larger than about 12 cm long, about 2.5 cm wide, and about 2.2 cm tall. However, any convenient shape may be employed, such as a credit card shaped reader. The device comprises a housing 2 formed from a light-impermeable synthetic plastics material (e.g. polycarbonate, ABS, polystyrene, high density polyethylene, or polypropylene or polystyrol containing an appropriate light-blocking pigment, such as carbon). At one end of the reading device is a narrow slot or aperture 4 by which a test strip (not shown) can be inserted into the reader.

On its upper face the reader has two oval-shaped apertures. One aperture accommodates the screen of a liquid crystal display 6 which displays information to a user e.g. the results of an assay, in qualitative or quantitative terms. The other aperture accommodates an eject mechanism actuator 8 (in the form of a depressible button), which when actuated, forcibly ejects an inserted assay device from the assay reading device.

The test strip for use with the reading device is a generally conventional lateral flow test stick e.g. of the sort disclosed in U.S. Pat. No. 6,156,271, U.S. Pat. No. 5,504,013, EP 728309, or EP 782707. The test strip and a surface or surfaces of the slot in the reader, into which the test strip is inserted, are so shaped and dimensioned that the test strip can only be successfully inserted into the reader in the appropriate orientation. The assay device and a surface or surfaces of the slot in the reader, into which the assay device is inserted, may also be so shaped and dimensioned that there is a precise three dimensional alignment of the reader and an inserted assay device, which ensures that the assay result can be read correctly the reader.

When a test strip is correctly inserted into the reader, a switch is closed which activates the reader from a "dormant" mode, which is the normal state adopted by the reader, thereby reducing energy consumption.

Figure 2:
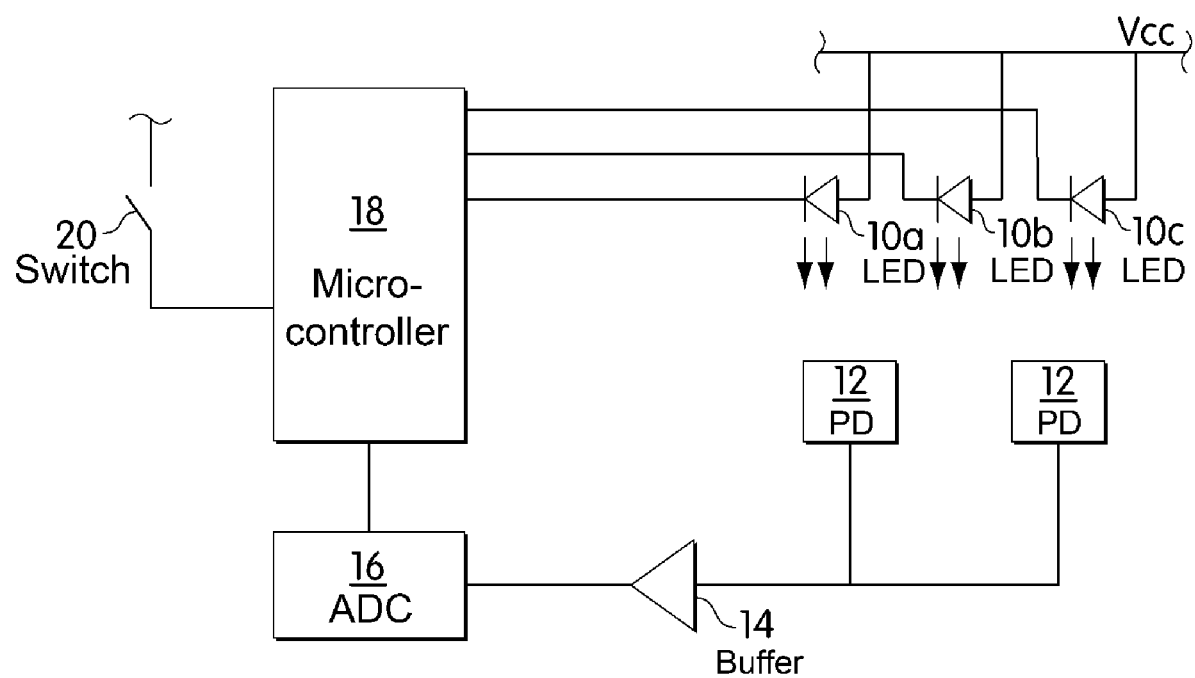
FIG. 2 is a schematic representation of some of the components of the embodiment illustrated in FIG. 1.

Enclosed within the housing of the reader (and therefore not visible in FIG. 1) are a number of further components, illustrated schematically in FIG. 2.

Referring to FIG. 2, the reader comprises three LED's 10a, b, and c. When a test strip is inserted into the reader, each LED 10 is aligned with a respective zone of the test strip. LED 10a is aligned with the test zone, LED 10b is aligned with the reference zone and LED 10c is aligned with the control zone. Two photodiodes 12 detect light reflected from the various zones and generate a current, the magnitude of which is proportional to the amount of light incident upon the photodiodes 12. The current is converted into a voltage, buffered by buffer 14 and fed into an analogue to digital converter (ADC, 16). The resulting digital signal is read by microcontroller 18.

In some embodiments, a separate photodiode is provided to detect from each zone (i.e. the number of photodiodes equals the number of zones from which reflected light measurements are made).

In other embodiments, such as that illustrated in FIG. 2, the number of photodetectors is less than the number of zones. One photodiode detects light reflected from the test zone and some of the light reflected from the reference zone. The other photodiode 12 detects some of the light reflected from the reference zone and the light reflected from the control zone. The microcontroller 18 switches on the LED's 10 one at a time, so that only one of the three zones is illuminated at any given time—in this way the signals generated by light reflected from the respective zones can be discriminated on a temporal basis.

FIG. 2 further shows, schematically, the switch 20 which is closed by insertion of an assay device into the reader, and which activates the microcontroller 18. Although not shown in FIG. 2, the device further comprises a power source (typically a button cell or two button cells), and an LCD device responsive to output from the microcontroller 18.

In use, a dry test strip (i.e. prior to contacting the sample) is inserted into the reader, this closes the switch 20 activating the reader device, which then performs an initial calibration. The intensity of light output from different LED's 10 is rarely identical. Similarly, the photodetectors 12 are unlikely to have identical sensitivities. Because such variation could affect the assay reading an initial calibration is effected, in which the microcontroller adjusts the length of time that each of the three LED's is illuminated, so that the measured signal from each of the three zones (test, reference and control) is approximately equal and at a suitable operating position in a linear region of the response profile of the system (such that a change in intensity of light reflected from the various zones produces a directly proportional change in signal).

After performing the initial calibration, the device performs a further, finer calibration. This involves taking a measurement ("calibration value") of reflected light intensity for each zone whilst the test strip is dry-subsequent measurements ("test values") are normalised by reference to the calibration value for the respective zones (i.e. normalised value=test value/calibration value).

To conduct an assay, a sample receiving portion of the test strip is contacted with the liquid sample. In this case of a urine sample for instance, the sample receiving portion may be held in a urine stream, or a urine sample collected in a receptacle and the sample receiving portion briefly (about 5-10 seconds) immersed in the sample. Sampling may be performed whilst the test strip is inserted in the reader or, less preferably, the strip can be briefly removed from the reader for sampling and then reintroduced into the reader.

Measurements of reflected light intensity from one or more (preferably all three) of the zones are then commenced, typically after a specific timed interval following insertion of the test strip into the reader. Desirably the measurements are taken at regular intervals (e.g. at between 1-10 second intervals, preferably at between 1-5 second intervals). The measurements are made as a sequence of many readings over short (10 milliseconds or less) periods of time, interleaved zone by zone, thereby minimising any effects due to variation of ambient light intensity which may penetrate into the interior of the reader housing.

Example 2

Figure 3:
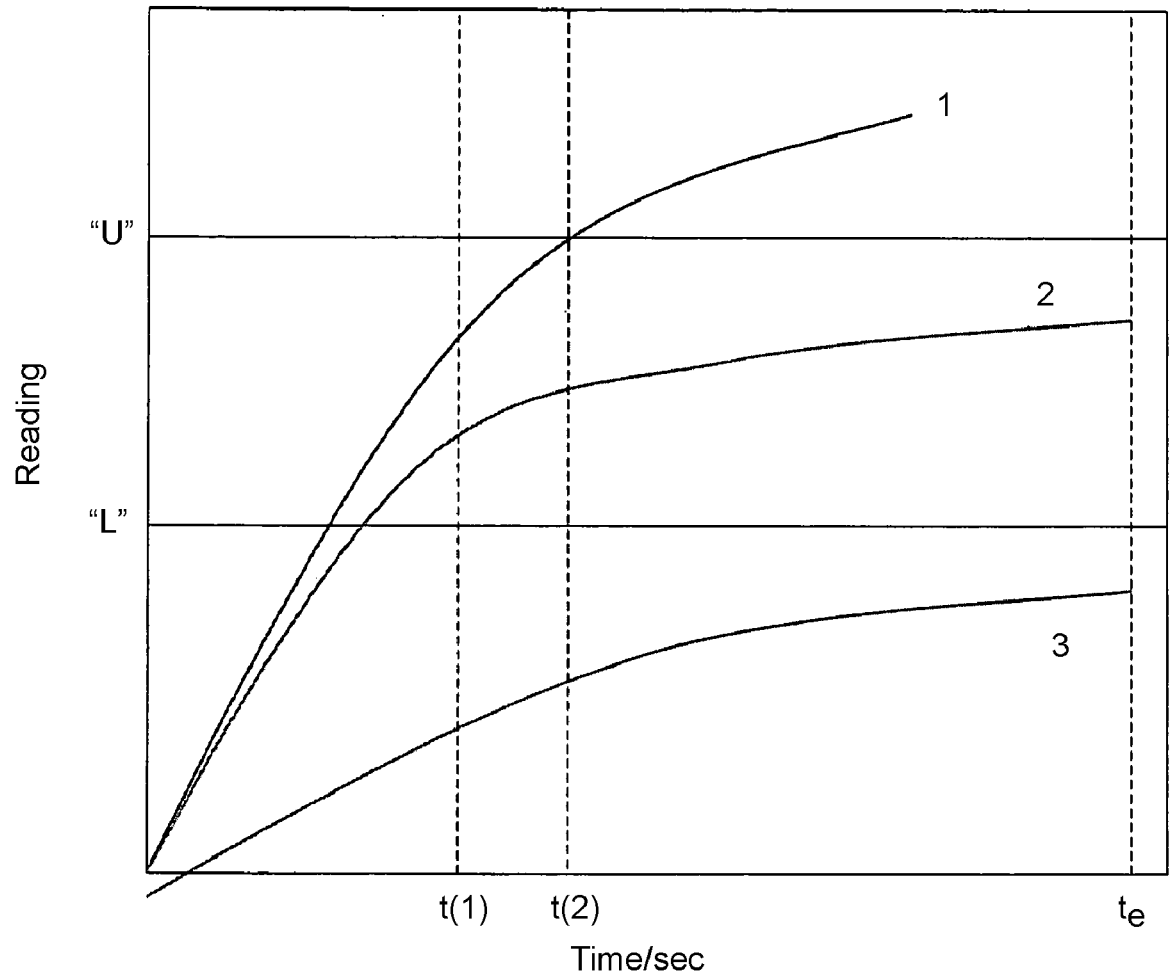
FIG. 3 is a graph of typical results for reading (i.e. signal) against time.

FIG. 3 shows typical results for three different samples, in terms of amount of signal ("Reading", in arbitrary units) against time (in seconds).

The amount of signal is a measure of the light absorbed, or the decrease in light reflected, from the test zone of a lateral flow test stick as might be determined using the assay result reader described in the preceding example. In the presence of the analyte of interest, a coloured particulate labelled binding reagent accumulates in the test zone. The coloured particulate label absorbs some of the light incident upon the test zone, and this reduces the amount of light reflected therefrom which is available for detection by a suitably positioned photodetector. The higher the concentration of analyte, the more rapid the rate of accumulation of label in the test zone and the stronger the "signal".

Plot 1 illustrates a typical graph which might be obtained for a liquid sample which contains a high concentration of analyte. Plot 3 illustrates a typical graph which might be obtained for a liquid sample which contains a very low concentration of analyte. Plot 2 illustrates a typical graph which might be obtained for a liquid sample which contains an intermediate concentration of analyte.

Also shown on the graph are two horizontal lines which indicate the upper threshold ("U") and lower threshold ("L") values respectively.

Referring to plot 1, the reader is programmed to make an initial reading at t(1), a certain predetermined length of time after commencement of the assay. The reading obtained is below the value of "U", so an early positive result cannot be declared at t(1).

Equally, the reading is above the value of "L", so an early negative result cannot be declared at t(1) either. In this situation, the reader is programmed to repeat the measurement after a further, predetermined period of time has elapsed, at t(2). At t(2) the reading for plot 1 has just exceeded the value of U, so the reader can promptly indicate that the result is positive, via the LCD device.

Referring to plot 3, at t(1) the initial reading is below the value of L, so the reader can promptly declare a negative result, since it can be predicted that the value will never exceed the upper threshold before the predetermined endpoint of the assay $t_e$.

Referring to plot 2, the initial reading at time t(1) is, similar to that for plot 1, below the value of U but above the value of L, so an early positive or negative result cannot be declared. The same is true at t(2). If desired, the reader can be programmed to make any number of further readings at t(3), t(4) etc. until the final reading is taken at $t_e$. For plot 2, the final reading at $t_e$ is still below the value of U, so the assay result would be negative.

The following comments apply generally, not just to the example described immediately above. It should be noted that, rather than measure absolute readings, values may be calculated with respect to the rate of change of reading with respect to time, or d(reading)/d(time). Alternatively, the rate of change of slope with respect to time may be measured or $d^2(reading)/d(time)^2$ or the integral $\int d(reading)$ with respect to two or more time values, namely the area defined by the curve. This has the advantage that reading is averaged over time, which smooths any anomalies. Alternatively, the rate of change of slope with respect to time may be measured or $d^2(reading)/d(time)^2$. As a further alternative, all or some of the above measurements may be made in combination to yield a result. Thus rather than provide an early result based upon the value of the reading exceeding a lower or upper threshold, the reader may make this evaluation based upon calculation of a first or second differential, an integral or combination of one or more thereof. Furthermore, an early result may be promptly declared after the reading has exceeded the lower threshold but the reader determines that the result will not exceed the upper threshold value before the reading has reached equilibrium Furthermore it may be noted that the values of the at least upper and lower threshold limits may be adjusted during the course of the assay reading. This may occur on the basis of the readings obtained earlier in the course of the assay. It is preferable however that these values remain constant during the course of an individual assay.

As an alternative to promptly declaring the result, the reader may wait for a certain defined period before declaring a result. This provides an extra control feature, such that for example a result is not declared before various control checks have been made on either the assay strip, the reader or both. Such a situation might occur for a sample having an exceedingly high or low analyte concentration.

Example 3

An assay result reading device was created for making pregnancy determinations based on the concentration of hCG in urine. The test strip includes anti-hCG antibody coupled to a chromophore.

The upper threshold was set at 10% attenuation gain (AG) (signal vs reference), and the lower threshold was set at 6% attenuation gain (control vs ref). 10% AG corresponds to approximately 15 mIU hCG for a new test-strip and 25 mIU for an aged test-strip (aging is believed to cause decay of the antibody, resulting in an apparent increase of signal) and 6% AG corresponds to approx. 5 mIU. In other embodiments, the upper threshold can be set between about 10 and about 90% AG, and the lower threshold between about 1% and about 9%, although in principle other value ranges could be chosen.

The initial time reference (t=0) is set when the control vs reference signal passes through zero. This means that the sample fluid has reached the control line. The timer is then started. The analyte signal is compared to the threshold values as described previously. The earliest time point for a positive (pregnant) result is set at 20 seconds, and the earliest point for a negative result is set at 60 seconds. In other embodiments, of course, other time periods may be set.

The disclosed devices and methods may, naturally, be adapted for use with a wide variety of analytes. In particular, it should be noted that the disclosed devices and methods may be used in situations in which a negative result is expected only in the absence of analyte, and also in situations where a negative result is appropriate even when the analyte is present in some amount. An example of the first situation is a test for a pathogen, such as HIV or strep A. However, even in the absence of analyte, a lower threshold is still set and threshold test employed, because non-specific binding may otherwise result in a false-positive background reading.

An example of the second situation is an assay result reader for ovulation that measures luteinizing hormone (LH), because LH is normally present at a basal level and surges shortly before ovulation; a positive result is desired during the surge, and a negative result during the basal level.

Example 4

The above-described examples refer to assay result reading devices that work as one-time tests; i.e., a single test strip is assayed for a single test result. The threshold values typically remain fixed from test to test for reliability and reproducibility.

However, some embodiments may employ a series of test strips in order to track the amount of an analyte over time, and to adjust the threshold values from strip to strip in the series order to provide precise results.

One example of such a system is an assay result reader that measures luteinizing hormone (LH) over several days to predict ovulation based on detecting the "LH surge" shortly before ovulation. In a typical procedure, a first measurement is made. If it is above a certain upper threshold (for example, greater than 16% AG), a positive result indicating "LH surge" is returned. If the measurement is below this threshold, then the upper threshold for the next test is adjusted, depending on the level measured. For example, if the signal is lower than 7% AG, the upper threshold is lowered to 13%. If the measurement for the first test-strip is lower than respectively 5% or 3%, values of respectively 12% and 11% are chosen.

Thus, the algorithm chooses the threshold on the basis of the previous day's measurement, but it could also be an average of the previous days measurements. Thus in general, the thresholds need not necessarily be fixed.

Example 5

In some embodiments, the assay result reading device includes a memory system that stores prior test results accumulated over a period of time. For example, the device may be configured for testing for the presence of a drug of abuse or a metabolite thereof, and the memory system can store periodic test results. The device also includes a system for viewing or retrieving test results, such as by a display, and electronic connection, or the like.

Example 6

In some embodiments, the assay result reading device includes a memory system that stores test profiles for a variety of analytes. A profile can include, for example, the upper threshold and the lower threshold. The profile can further include time periods for performing threshold comparisons. In this manner, a single assay result reading device may be used to perform a variety of analyte assays.

The device further includes a selection system that selects the appropriate profile for the desired analyte. In some embodiments, the selection system can be a switch that a user sets to the desired test. In other embodiments, the selection system detects a feature on an assay test strip indicative of the analyte to be measured. For example, the test strip may have a bar code or other optical pattern. Alternatively, a test strip may be configured so that it remits light of a certain frequency or in a frequency range that is characteristic for a particular analyte. The memory system has a look-up table that the selection system may access to identify an analyte based on the remitted light frequency.

Example 7

An assay result reader according to the present disclosure may also include a system for detecting flow rate of a fluid sample, such as one described in U.S. patent application Ser. No. 10/742,459, filed Dec. 19, 2003.

Example 8

An assay result reader according to the present disclosure may also include optical arrangement such as those described in U.S. Patent Application Ser. No. 60/508,001, filed Oct. 2, 2003.

Figure 4:
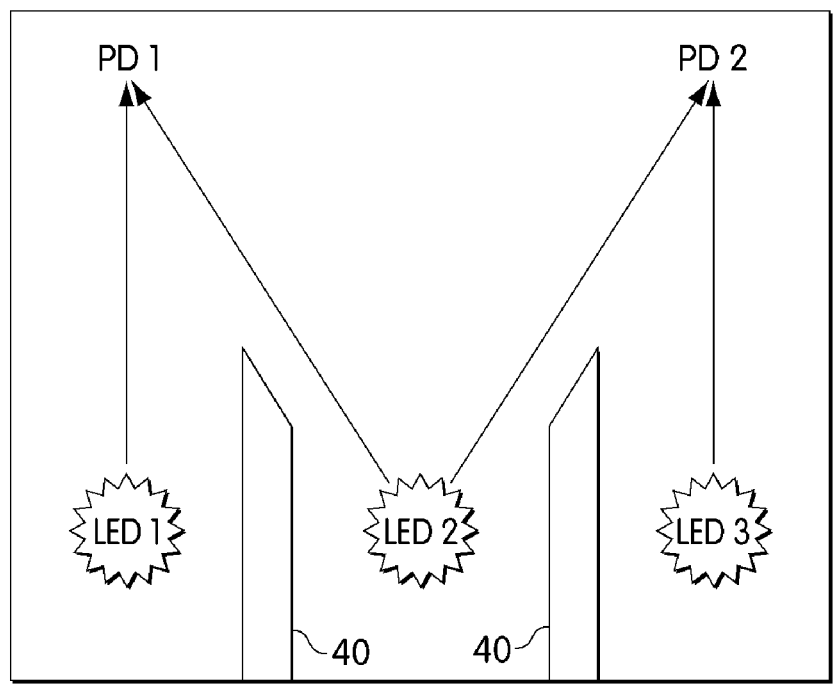
FIGS. 4-6 are schematic representations of an embodiment incorporating a preferred light source/photodetector arrangement.
Figure 5:
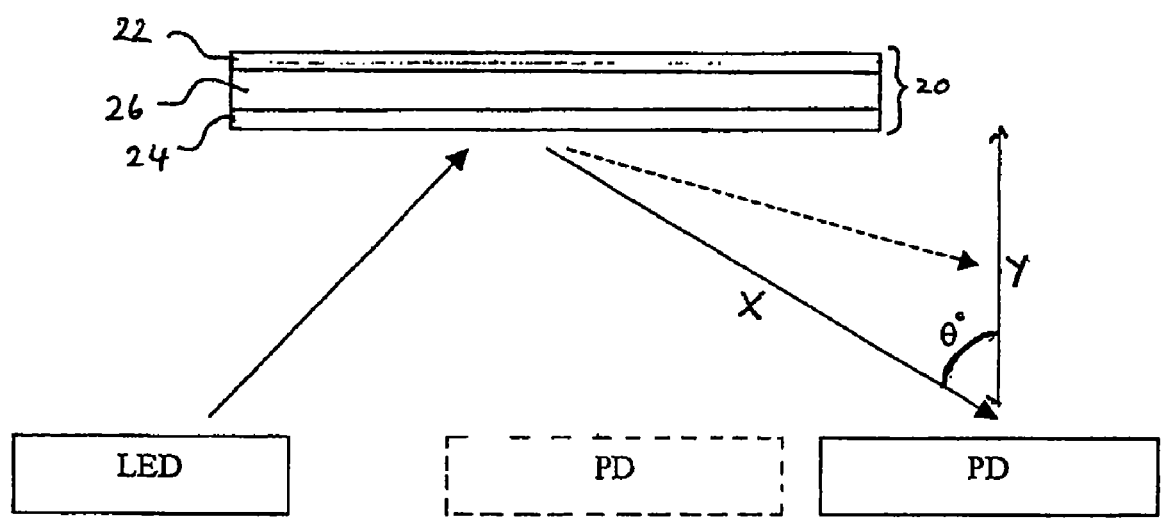
Figure 6:
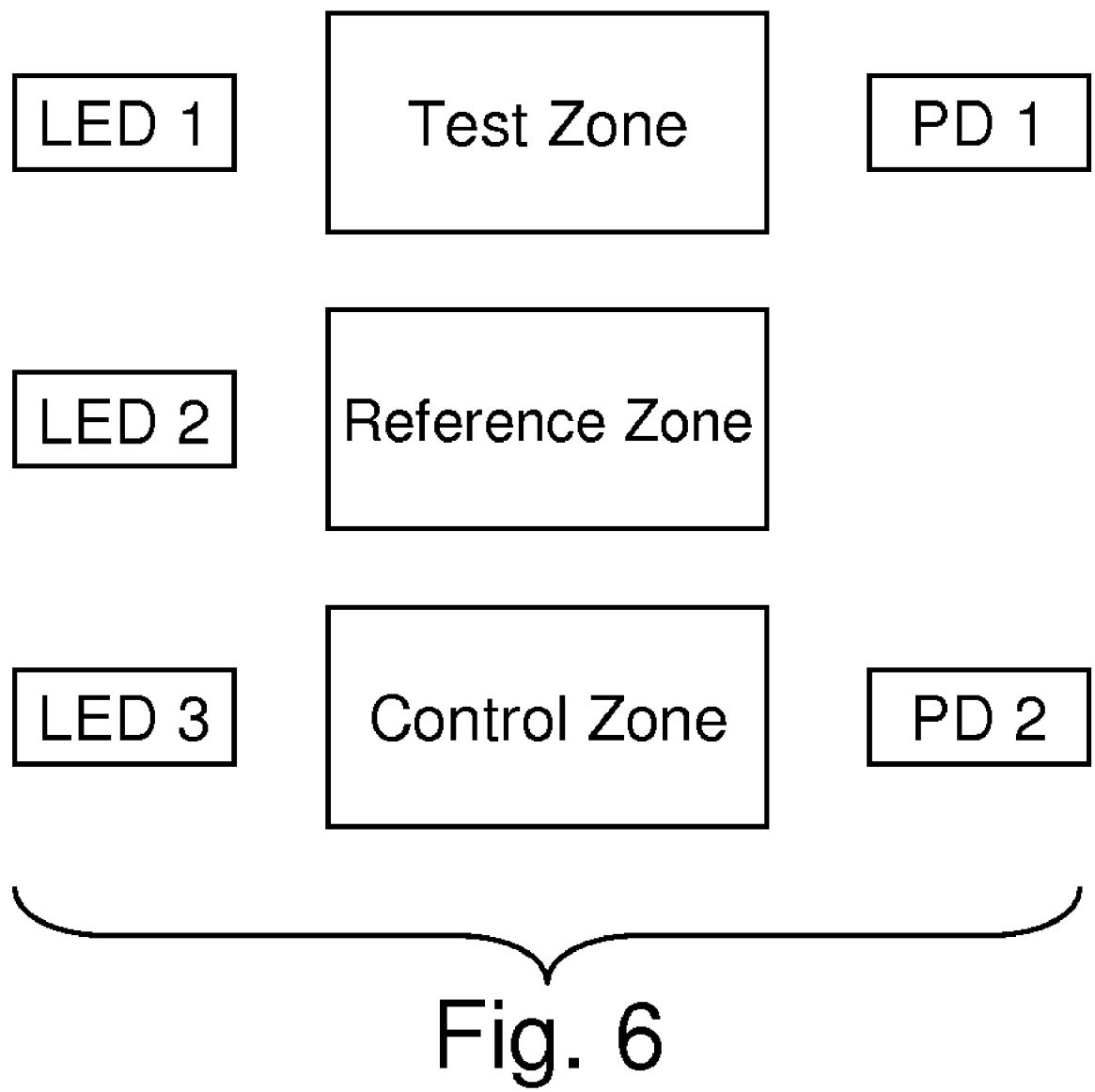

FIG. 4 is a schematic representation of the layout of the 3 LED/2 Photodiode optical system described in Example 1. FIG. 5 is a schematic representation of a side elevation of one LED/Photodiode, and illustrating their position relative to a nitrocellulose test strip. FIG. 6 is a schematic plan view of the LED/Photodiode arrangement, again illustrating their position relative to a test strip.

Referring to FIG. 4, an optics block component for accommodation within an assay result reading device may include three LEDs (LED 1, 2 and 3) and two photodetectors (PD1 and PD2). Light from LED 1 illuminates a test zone of a test strip (not shown) inserted into the reader. Light reflected from the test zone is detected by PD1. Light from LED3 illuminates a control zone of the test strip and light reflected therefrom is detected by PD2. Light from LED2 illuminates a reference zone of the test strip.

Each LED is optically isolated by light-impermeable baffles 40, which ensure that the various LEDs are capable of illuminating only its respective zone of the test strip. However the surfaces of the baffles facing LED2 are angled so as to allow LED2 to illuminate a slightly wider portion of the test strip than LED1 or 3, and this in turn allows light reflected from the reference zone to be detected by both PD1 and PD2.

The relative positioning of the test strip, LEDs and photodiodes may be better understood by reference to FIGS. 5 and 6.

Referring to FIG. 5, a test strip 20 is inserted into the reading device above the plane of the LEDs and photodiodes. The test strip 20 is of laminate construction including an uppermost backing layer 22 of reflective opaque white MYLAR®, a synthetic plastics material, and a lowermost front layer 24 of clear MYLAR®. Sandwiched between the MYLAR® layers 22, 24 is a layer of porous material 26 (typically nitrocellulose). The purpose of the MYLAR® layers is to protect the delicate nitrocellulose and provide mechanical strength and rigidity. In addition, the opaque backing layer 22 is relatively highly reflective, and this serves to improve contrast: relatively little light is absorbed by the layers 24, 26 and much of the light incident upon the various zones would therefore tend to pass straight through the test strip, but the reflective MYLAR® backing layer 22 ensures that this light is reflected. In addition, since the particulate label accumulating in the nitrocellulose layer 26 absorbs only a portion of the light as it passes through in a generally upwards direction, the label has in effect a second chance to absorb light as it passes back through the test strip 20 in a generally downwards direction, having been reflected by the opaque MYLAR® backing layer 22. This significantly improves the signal-to-noise ratio.

As can be seen from FIGS. 5 and 6, the photodiodes PD1 and PD2 are aligned with their respective LEDs, LED1 and 3, but are offset, in that the LEDs lie towards one side of the test strip while the photodiodes lie towards the other side. Having the photodiodes offset in this way avoids, or at least reduces, the amount of specular reflection from the clear MYLAR® layer 24 detected by the photodiodes (i.e. light which is reflected directly from the initial MYLAR® layer 24 without ever penetrating into the nitrocellulose layer-detection of such reflections would decrease the signal:noise ratio).

Referring to FIG. 5 the relationship between signal intensity (I) and the angle (θ) of the reflected light relative to the photodiode is $I \propto \cos \theta^4$. Furthermore, the relationship between signal intensity (I) and the distance (x) of the photodiode from the reflecting object is $I \propto 1/x^2$ (i.e. the inverse square law). It is apparent that, in view of the inverse square law, it would generally be preferred to position the photodiodes as close as possible to the test strip (i.e. decrease x), so as to increase the signal intensity I. However, merely decreasing the vertical separation y between the photodiode and the test strip would increase angle θ, decreasing the value of cos θ and therefore tend to reduce the signal intensity.

An alternative approach to improve signal intensity would be to re-position the photodiode nearer the center of the system (indicated by the dotted lines in FIG. 5) which would simultaneously decrease x and θ. However, this is found to be undesirable as it increases the likelihood of detecting specular reflections. Accordingly an aligned but offset position for the photodiodes provides an optimal compromise of the considerations.

It may be noted from FIG. 6 that photodiode 1 is aligned with the test zone and photodiode 2 is aligned with the control zone. This alignment ensures that any variation of the relative positioning of the test strip and assay reader has minimal effect on the angle θ. While PD1 and PD2 are not aligned with the reference zone, and are therefore subject to a relatively large (and therefore undesirable) angle of θ, this problem is not significant because (i) the use of two detectors to read the reference zone allows for compensation of any positional variation, since relative movement of the test strip so as to increase θ for one photodetector may decrease θ for the other photodetector; and (ii) the reference zone is used to give a background reading for calibration purposes—the photodiodes are not required to measure the signal intensity from a narrow line (as with the test or control zones), and so the measurement of the reference zone signal is inherently less sensitive to variation from mis-positioning.

Example 9

This example described in greater detail the features of the preferred arrangement of LED's and photodiodes outlined in Example 1.

Figure 7:
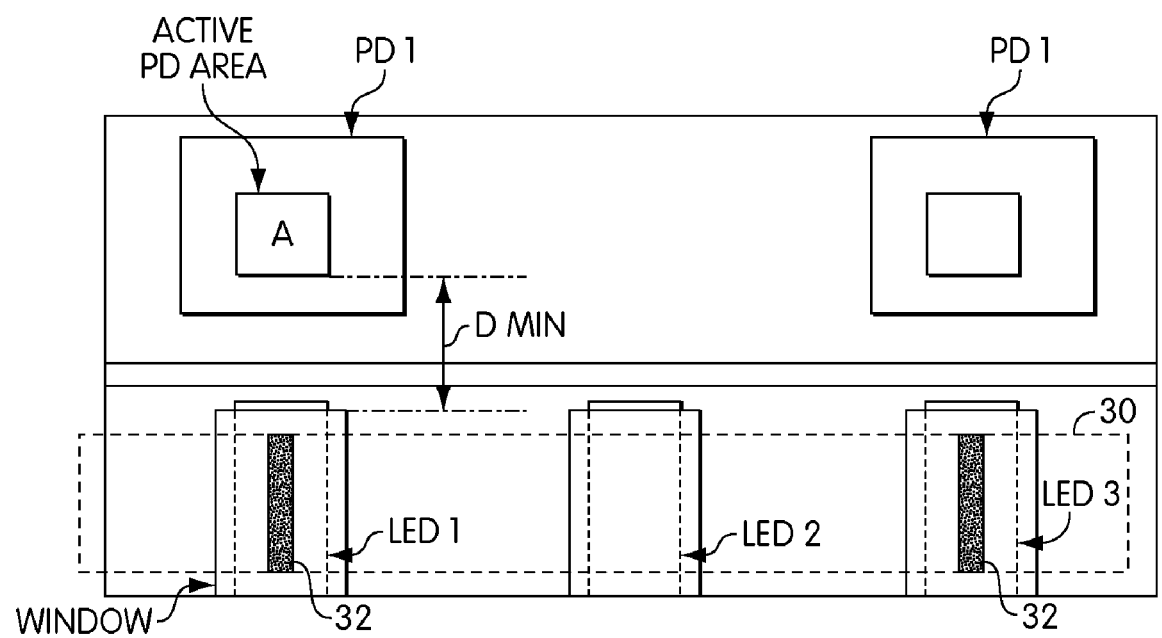
FIG. 7 is a plan view of certain internal components showing an embodiment of one arrangement.

FIG. 7 shows a plan view of an exemplary embodiment of an optical arrangement. In this embodiment, the optical arrangement include three light emitting diodes and two photodetectors. The active area (A) of the photodetectors (PD) is 1.5 mm×1.5 mm. The optics are arranged such that center lines of LED's 1 and 3 correspond to the center lines of PD1 and PD2. The 3 LED's and two photodetectors are disposed within an area no larger than about 1 square cm, preferably no larger than about 0.7 square cm, specifically 1 cm×0.7 cm.

Also shown is the position of the test-strip 30 that is positioned above the LED's. The test-strip is inserted so that the test and control lines 32 are situated above respectively LED's 1 and 3. The distance D, namely the distance between the PD and LED, is preferably large enough to prevent specular reflection of light emitted from the LED from the surface of the test-strip directly to the PD. This distance will be dependent upon various factors such as the size of the windows, as well as the distance between the windows and the LED's and will be best determined by routine experimentation. The windows are situated above the respective LED's that effectively define the areas through which light shines. In one exemplary embodiment, the dimensions of the window are 2 mm wide by 2.75 mm high.

Figure 8:
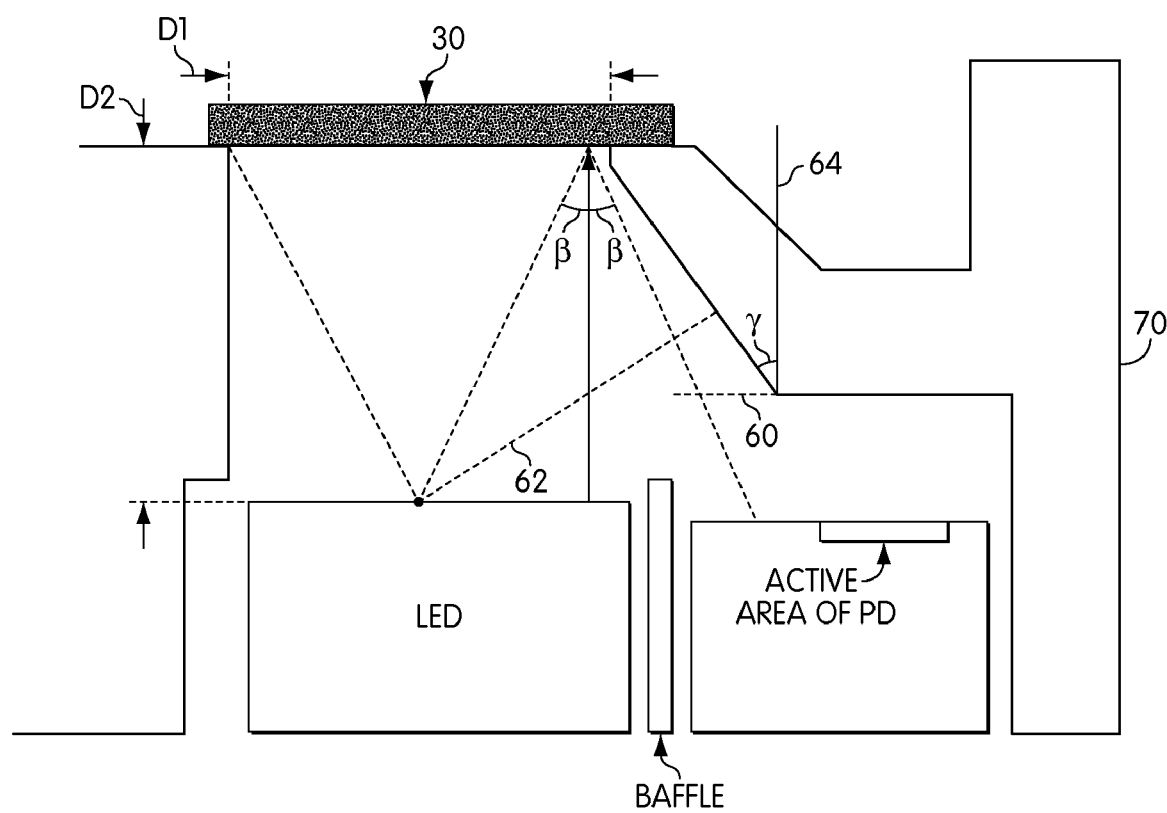
FIG. 8 is an elevation view of certain internal components showing an embodiment of one arrangement and exemplary optical paths.

FIG. 8 shows the spatial relationship between the LED and photodiode. The photodiode is positioned at a sufficient distance to ensure that it does not receive specular reflections from the front cover of the test-strip 30. Specular reflections are a direct reflection. Thus any light hitting the test-strip at an angle β will also reflect at the same angle. Thus to avoid the PD detecting specular light, it is offset. The degree of offset is dependent upon the height D2, the window opening width D1.

The substrate 70 supporting the window is made from black plastic and is chosen to be at a particular angle γ. If the plastic were constructed so as to have a horizontal roof (as denoted dashed line 60), light from the LED could bounce of the roof and onto the PD. To avoid this the substrate is angled such that light hitting the angled part reflects directly back (as denoted by dashed line 62). Again this angle is dependent upon D1 and is approx 40% in the device shown by reference to the solid line 64.

Finally the height of the divide is chosen to be a certain height such that light from the LED does not shine directly to the PD. The height of the divide will be determinant upon the height of the LED. In one exemplary embodiment, the LED height is 1.5 mm and the divide height 2 mm.

In a preferred embodiment the test strip comprises of a layer of a porous carrier such as nitrocellulose sandwiched between two layers of plastic such as MYLAR®. The layer proximal to the light source must be permeable to light, preferably transparent. In the situation wherein the PD's and LED are situated on the same side of the test-strip the layer distal to the light source must be capable of reflecting light. It is preferable for this distal layer to be white to increase contrast and hence the signal to noise ratio.

It is apparent that, in view of the inverse square law, it would generally be preferred to position the photodiodes as close as possible to the test strip (i.e. decrease x), so as to increase the signal intensity I. However, merely decreasing the vertical separation y between the photodiode and the test strip would increase angle θ, decreasing the value of cos θ and therefore tend to reduce the signal intensity.

An alternative approach to improve signal intensity would be to re-position the photodiode nearer the center of the system, which would simultaneously decrease the reflection distance and the angle of reflection. However the distance must be minimized to ensure that the maximum intensity of light is detected (the intensity decreases as a function of the distance of the PD from the test-strip and the angle of reflection).

Example 10

In one exemplary embodiment, the active area of the photodetector is 2 mm×2 mm. The light source provides light, at least some of which has a wavelength of 635 nm. The height of the test-strip above the light source is 5.5 mm. The wall height separating the LED's is 2.7 mm and the angle of the wall is 30 degrees. The plastic used is black nylon.

Example 11

FIGS. 9-14 illustrate an exemplary embodiment of portions of an assay reader.

Figure 9:
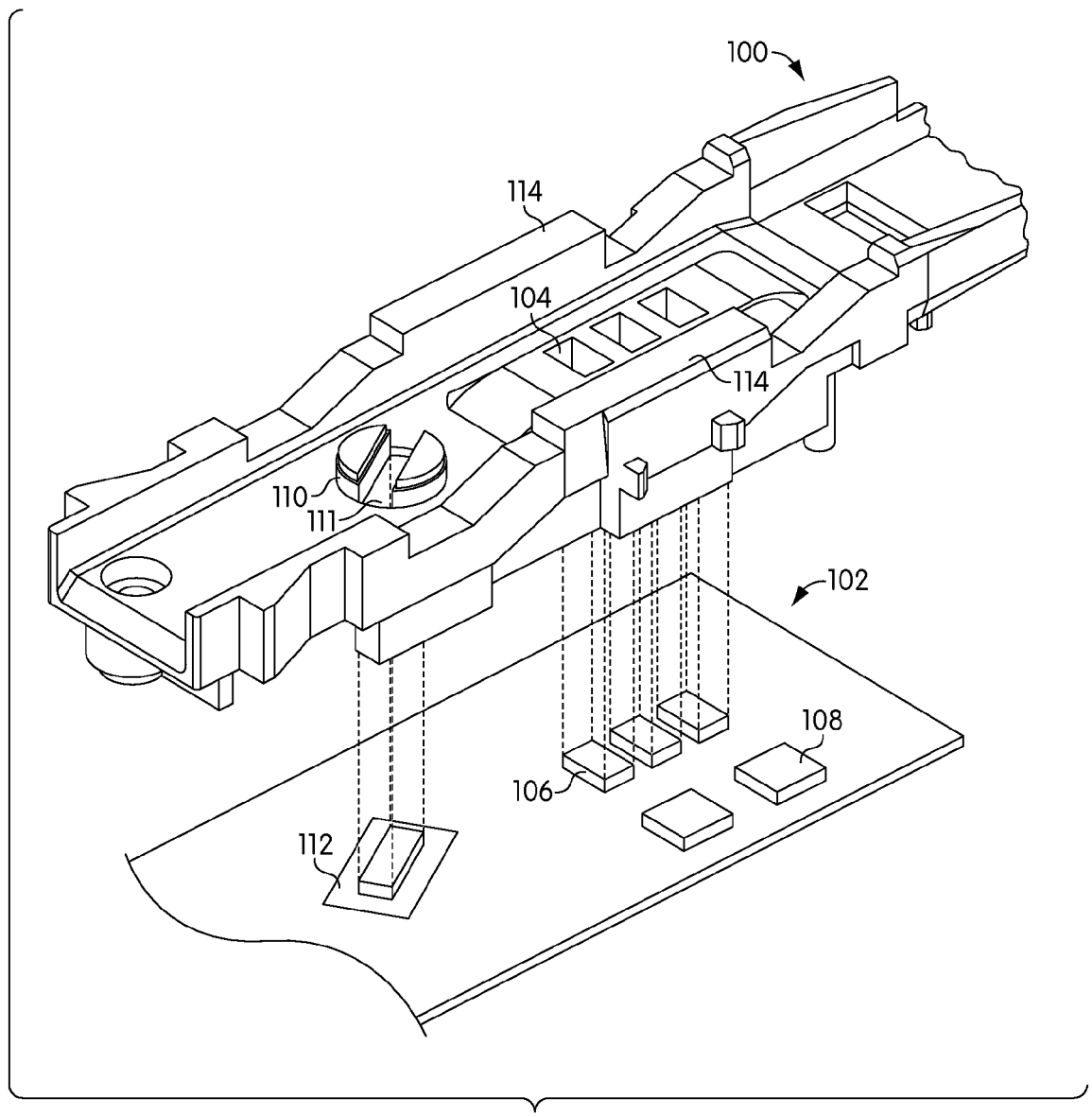
FIG. 9 is an exploded top perspective view of a baffle element and a circuit board of an exemplary embodiment.

FIG. 9 shows an exploded view of a baffle arrangement 100 and a printed circuit board (PCB) 102 that may receive the baffle arrangement. The baffle arrangement defines three windows 104 and includes a location feature 110 which may define an aperture 111 or some other feature that can engage a corresponding feature 112 on the PCB. The location feature 110 may also be so sized and shaped as to engage a mating feature on a test strip (not shown) when the test strip is introduced to the baffle arrangement. The strip may thus be locked into position during an assay measurement. The baffle arrangement also includes parallel raised side walls 114 that may guide the test strip into the correct location and ensure that it both engages with the location feature and is correctly linearly aligned with the windows 104 and not skewed. The PCB includes, among other item not shown, light sources such as light emitting diodes (LED's) 106 and light detectors such as photodiodes (PD's) 108. The LED's and PD's may be mounted in the same plane and positioned under the respective windows 104 such that light emitted from one or more LED's is able to pass through the window spaces onto the test-strip and be reflected back down onto one or more of the PD's.

Figure 10:
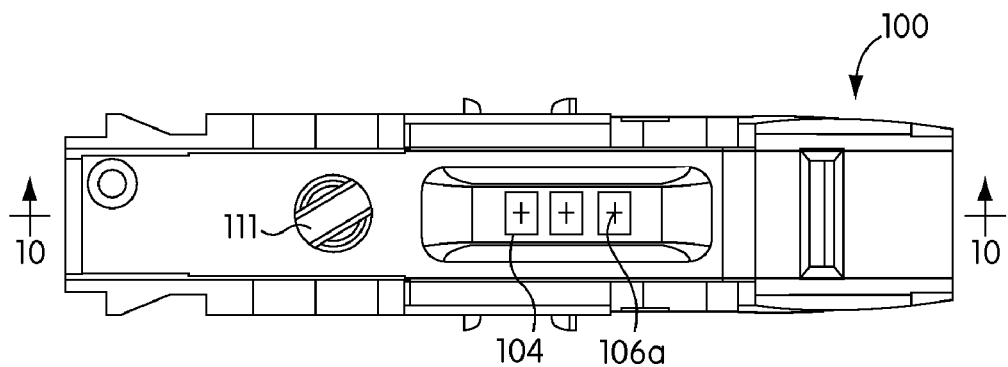
FIG. 10 is a top plan view showing an exemplary baffle arrangement.

FIG. 10 shows a top plan view of an exemplary embodiment of a baffle arrangement 110 in which the light source centers 106a are aligned under their respective windows 104.

Figure 11:
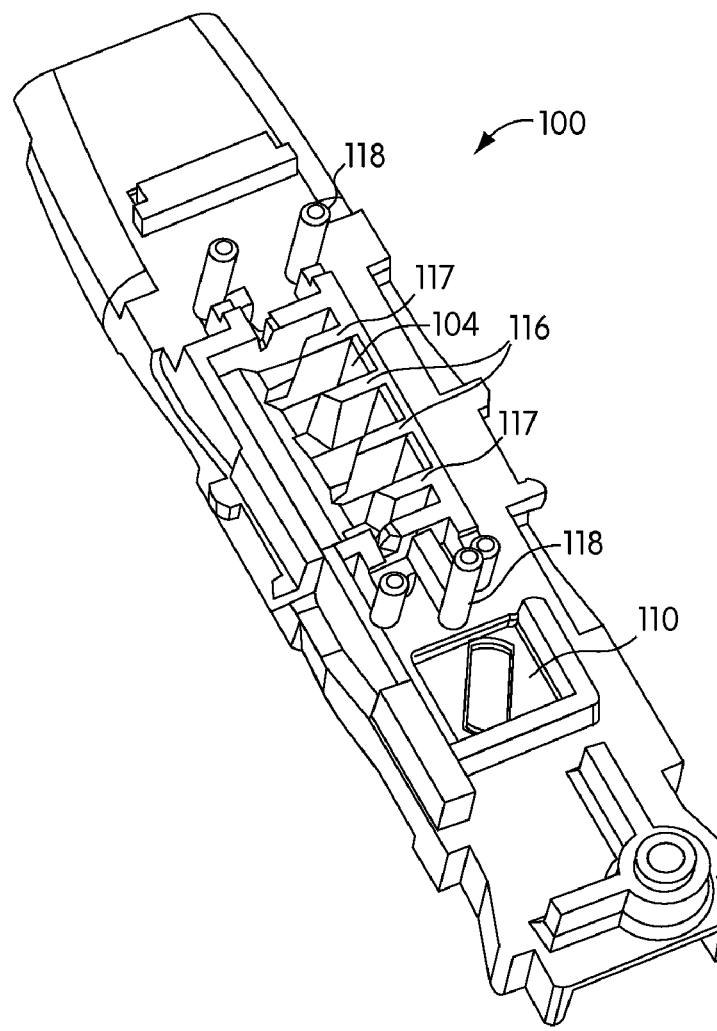
FIG. 11 is a bottom perspective view showing an exemplary baffle arrangement.

FIG. 11 provides an underside view of baffle arrangement 100. The arrangement may include a number of mounting pins 118 to provide contact points with the PCB (not shown). Defining windows 104 are baffles 116 and side barriers 117 that have angled walls to screen light as described above.

Figure 12:
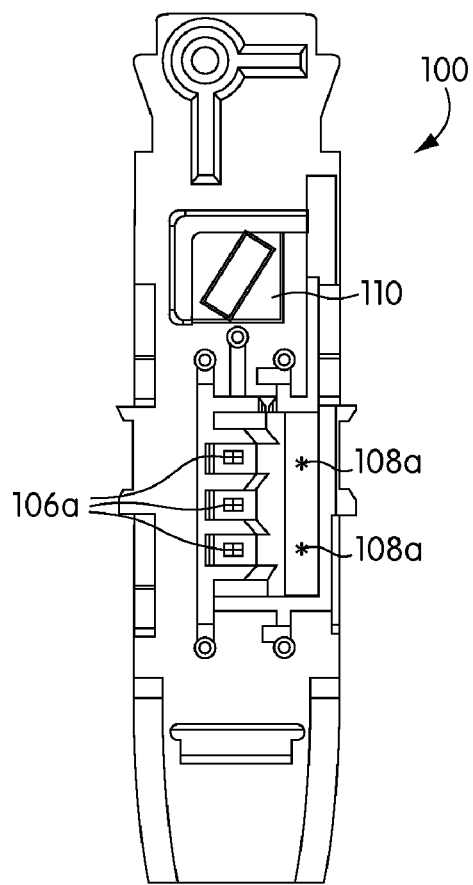
FIG. 12 is a bottom plan view showing an exemplary baffle arrangement.

FIG. 12 shows a bottom plan view of the baffle arrangement 100. The light source centers 106a are aligned under windows 104, and light detector centers 108a are offset to provide the appropriate incident angle, as described above.

Figure 13:
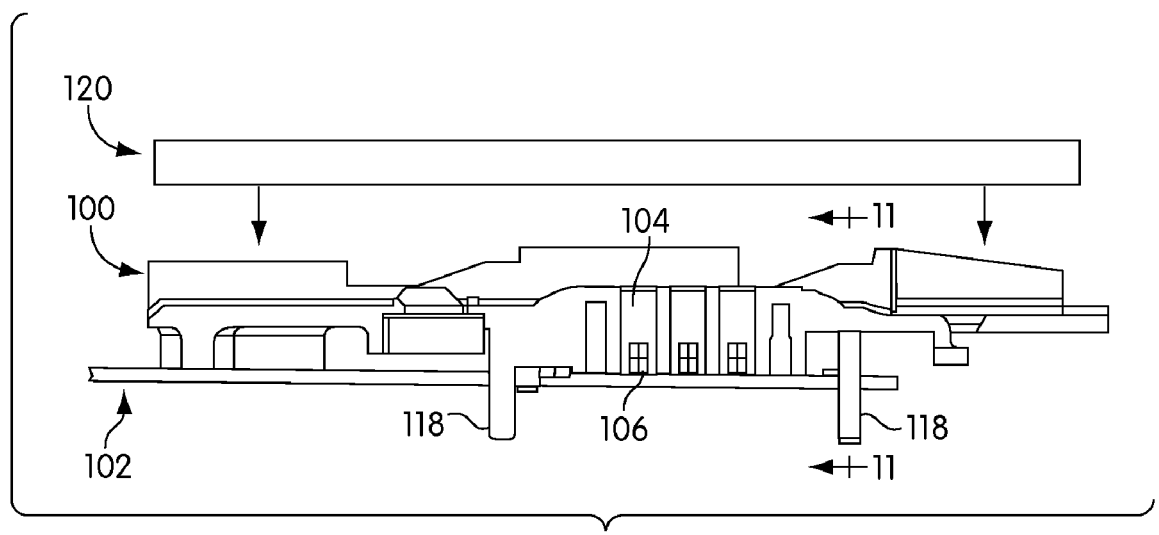
FIG. 13 is an exploded cross-sectional side view taken at line 10-10 in FIG. 10 showing an exemplary baffle arrangement, circuit board, and a test strip.

FIG. 13 depicts a longitudinal cross-section (taken at line 10-10 in FIG. 7) of baffle arrangement 100 seated on PCB 102 and a test strip 120 raised from its normal position in the baffle arrangement. The light sources 106 are positioned in their respective windows 104.

Figure 14:
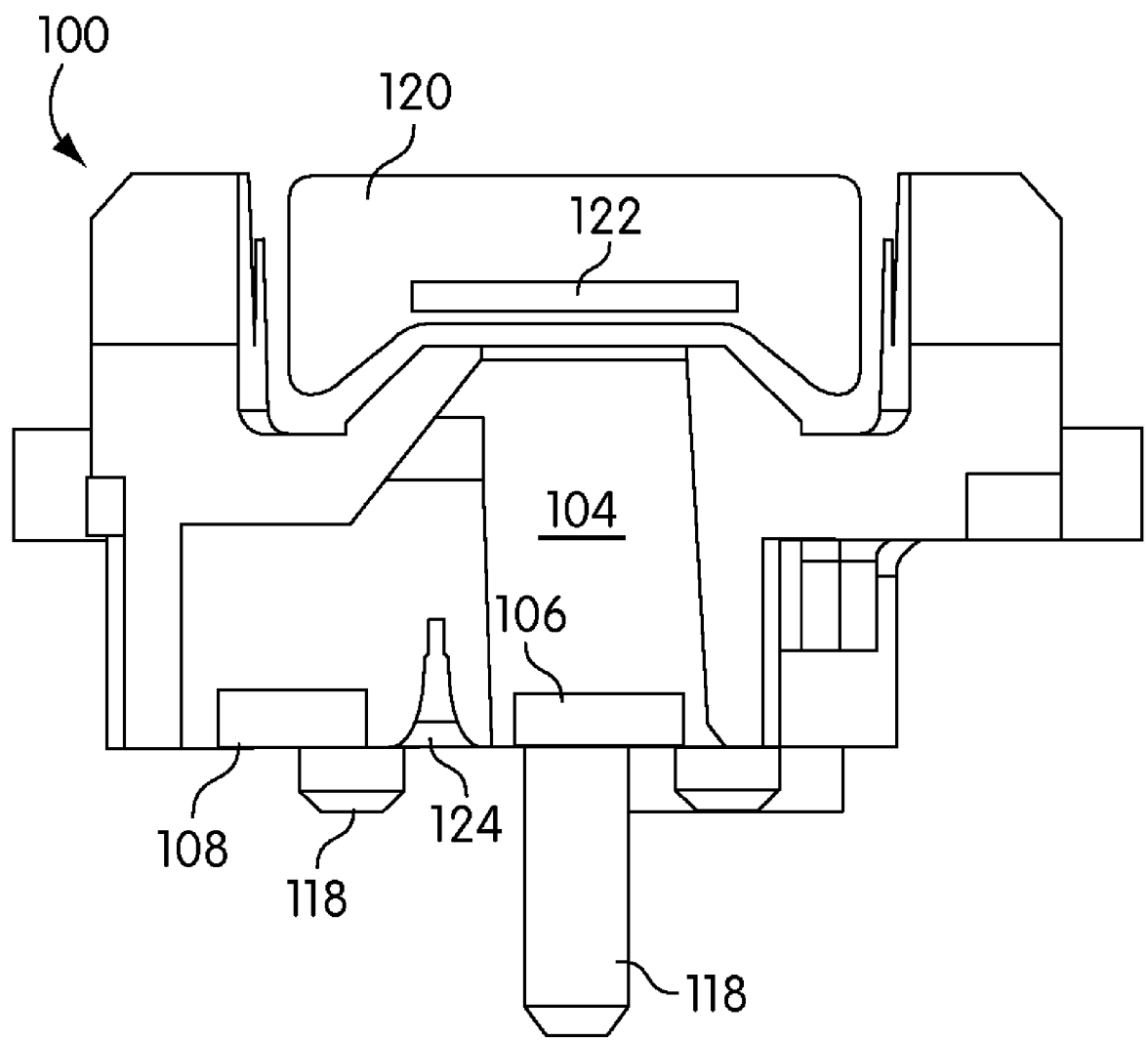
FIG. 14 is a transverse cross-sectional view taken at line 11-11 in FIG. 13 showing an exemplary baffle arrangement and a test strip.

FIG. 14 is a transverse cross section (taken at line 11-11 in FIG. 13) showing the test strip 120 in position relative to the baffle arrangement 100. The strip includes a porous carrier membrane 122 in which the assay reaction is conducted. Light emanative from a light source 106 impinges on the membrane. Light emanating from the membrane is detected by the light detector 108. A divider 124 prevents light from source 106 from shining directly on detector 108.

Example 12

An assay result reader according to the present disclosure may also include a system for declaring the result of an assay before completion of the assay, if a analyte measurement signal is above an upper threshold or below a lower threshold. Such systems are described in U.S. patent application Ser. No. 10/741,416, filed Dec. 19, 2003.

Example 13

An assay result reader according to the present disclosure may also include a system for detecting flow rate of a fluid sample, such as one described in U.S. patent application Ser. No. 10/742,459, filed Dec. 19, 2003.

Example 14

An assay result reader according to the present disclosure may further include both an early declaration system described in U.S. patent application Ser. No. 10/741,416 and a flow rate detection system described in U.S. patent application Ser. No. 10/742,459.

Example 15

Figure 15:
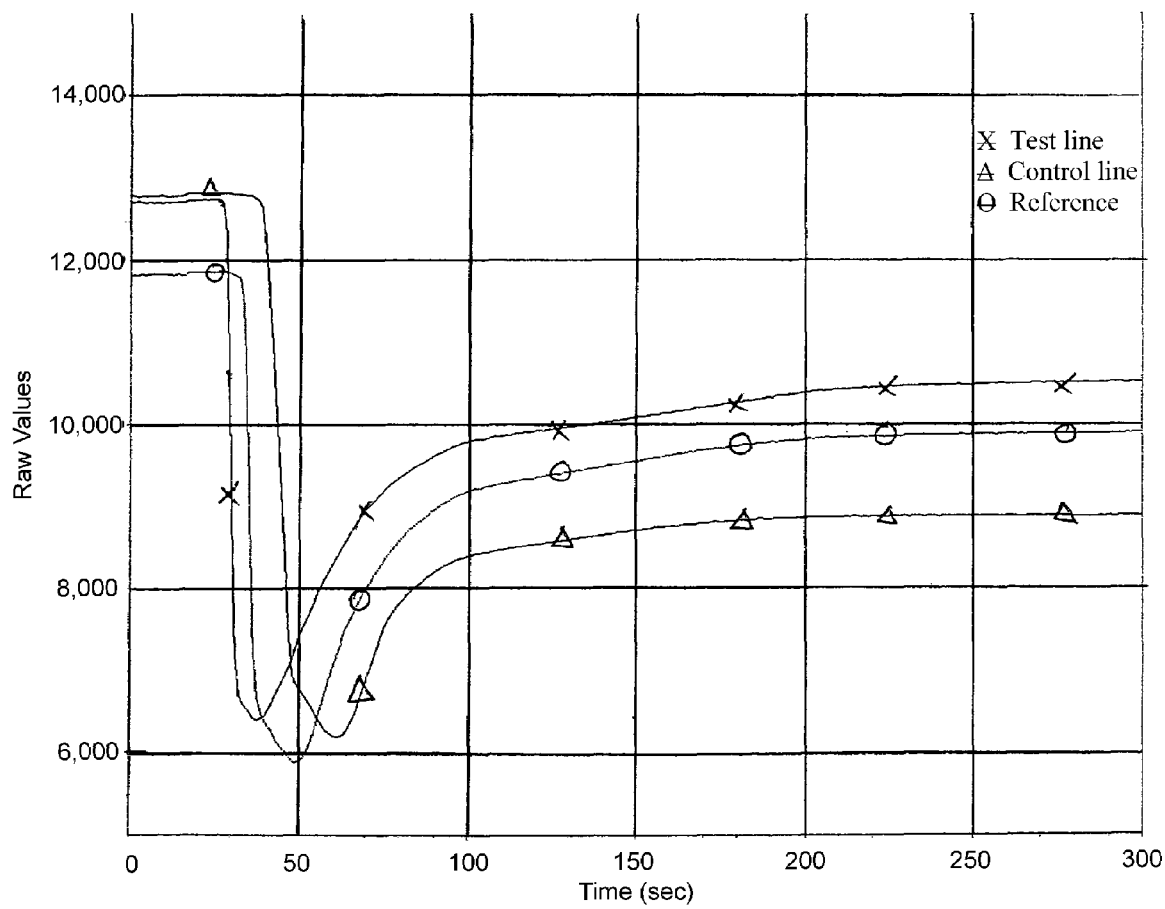
FIGS. 15-17 are graphs showing various signals returned from different portions of a test stick, inserted into the reading device illustrated in FIGS. 1-2, and their variation with time.

FIG. 15 is a graph showing the intensity of reflected light (arbitrary values) against time detected from each of the three zones, using a sample which does not contain the analyte of interest. The profile for the test zone is indicated by crosses, that for the reference zone by circles, and that for the control zone by triangles.

Considering the test zone profile, there is an initial lag phase during which the liquid sample is migrating along the porous carrier. In this period, the level of light reflected by the test zone is essentially constant. As the sample reached the test zone the amount of light reflected sharply decreases. This is primarily due to absorption of light by the coloured particulate label transported by the liquid sample. However some of the reduction in reflected light intensity is simply due to wetting of the nitrocellulose porous carrier, since dry nitrocellulose is more reflective.

As the fluid front moves past the test zone the level of reflected light starts to increase, the coloured label being transported with the sample downstream past the test zone. The reflected light intensity does not return to the original level because of the wetting of the nitrocellulose and because a small amount of the coloured particulate label is left behind as the liquid advances.

Generally similar profiles are exhibited by the reference and control zones, although these are downstream of the test zone and so lag further behind. The control zone profile, in particular, does not return to its original level of reflected light intensity because of development of the "control line" (i.e. deposition of coloured particulate label in the control zone).

Figure 16:
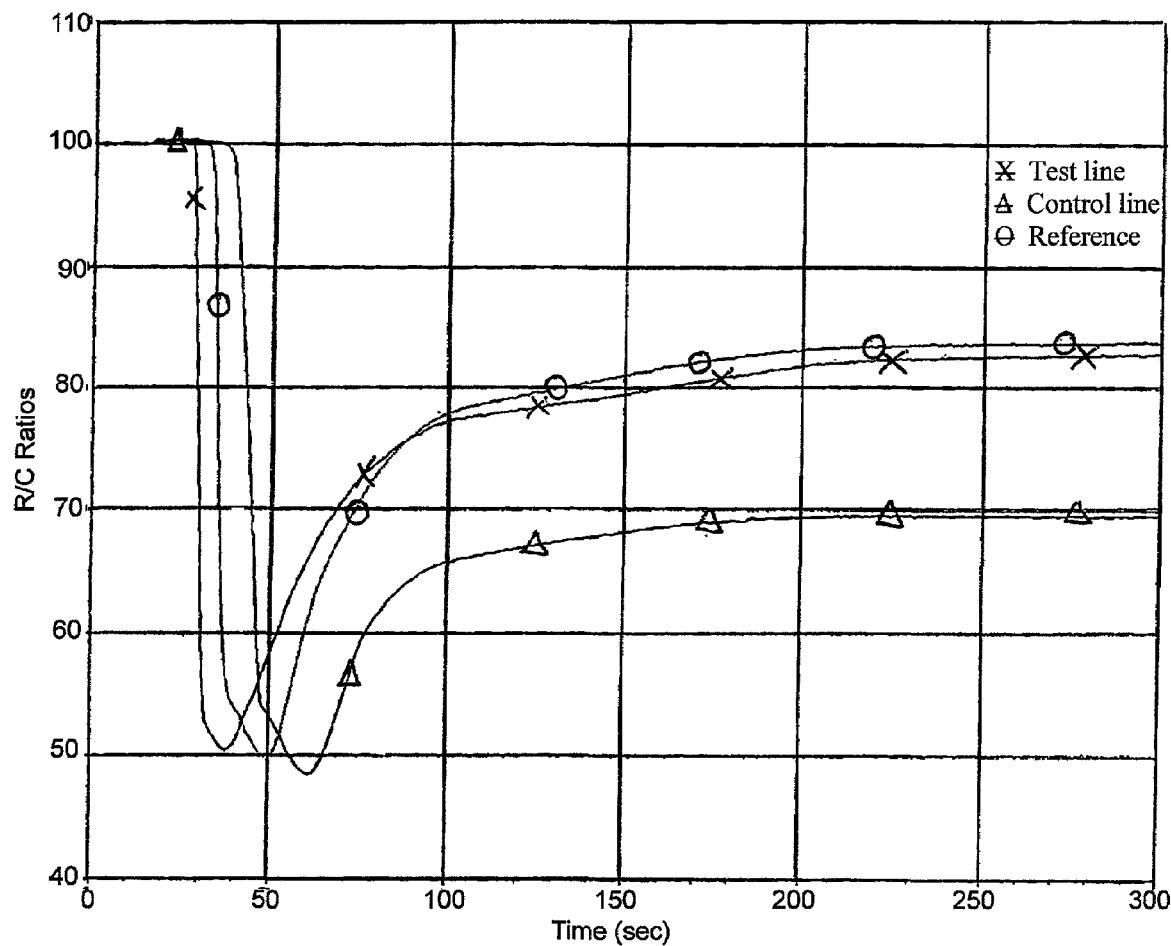

FIG. 16 is essentially similar, and shows the profiles obtained using % normalised results (i.e. test value divided by calibration value ×100). The profile being expressed in terms of % of calibration value against time. FIG. 16 demonstrates that normalisation of the test readings against an initial calibration reading reduces the variation in signal from the test, reference and control zones (although again the control zone value remains low due to the deposition of labelled reagent in the control zone).

In order to calculate the flow rate of the liquid sample along the porous carrier, the exemplified reading device actually compares the normalised results from the test and control zones with the result obtained from the reference zone in order to arrive at a "Relative attenuation of reflected light intensity" (% A).

$$\left[ \% \ A = \frac{(Ref(t)/Ref(\text{cal}) - Test(t)/Test(\text{cal})}{Ref(t)/Ref(\text{cal})} \right]$$

Figure 17:
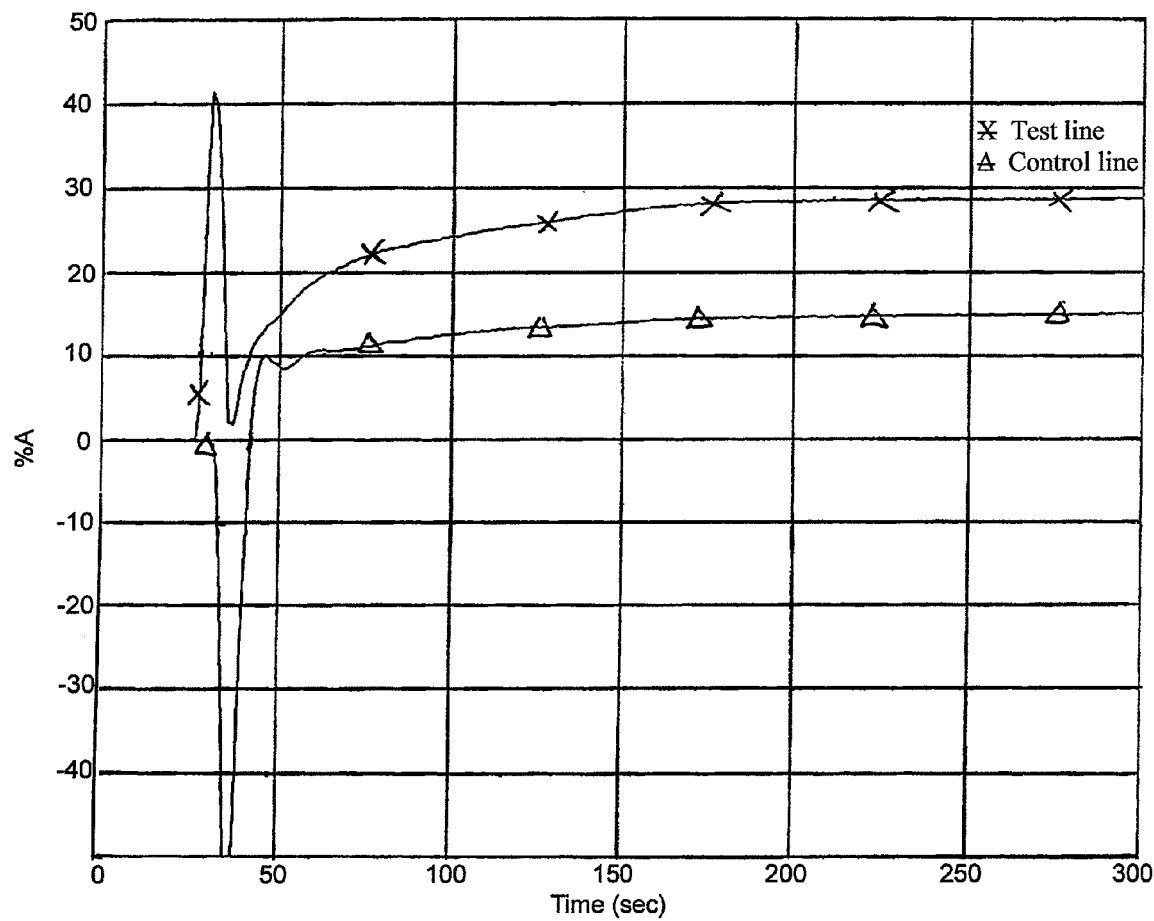

Typical % A profiles (against time), for a sample containing a relevant analyte of interest, are shown in FIG. 17. A positive attenuation means that the zone in question is reflecting less light than the reference zone, whilst a negative attenuation means that the zone in question is reflecting more light than the reference zone.

Referring to the % A profile of the test zone, it is apparent that the test zone signal is initially greatly attenuated (relative to the reference zone) when the liquid sample (with coloured particulate label) reached the test zone, but has not yet reached the reference zone. After about 35 seconds, the liquid sample starts to reach the reference zone and this leads to a sudden drop in the relative attenuation of the test zone. After about 40 seconds, the fluid front starts to leave the reference zone leading to an increase in the reflectivity of the reference zone and therefore an increase in the relative attenuation of the test zone. This levels off and eventually reaches a plateau, at a positive attenuation of just under 30%, the test zone having captured some of the coloured particulate label due to the presence in the sample of the analyte of interest.

Considering the profile for the control zone, it is apparent that there is an initial sharp fall (negative attenuation), since the liquid sample reaches the reference zone before the control zone. As the liquid sample starts to leave the reference zone before the control zone the relative negative attenuation in signal from the control zone starts to return to zero, and as the liquid samples reached the control zone the relative attenuation becomes positive and reached a plateau level of about 15%, due to the deposition of labelled reagent in the control zone to provide a positive control result.

Whilst in the presently exemplified reader the test zone result is compared with the reference zone result, a useful alternative would be to compare the test zone result with the control zone result.

In general terms the flow rate is calculated by detecting the change in reflected light intensity associated with the arrival of the liquid sample at a particular zone, and determining the time which elapses between the arrival of the liquid sample at the various zones. More precisely, the flow rate is calculated as described below.

The signal at all three zones is measured irrespective of the position of liquid on the test strip.

The signal attenuation at the test zone is measured with respect the signal attenuation at the reference zone. When the fluid front arrives at the test zone the signal attenuation will change relative to the reference zone, due to the fluid front not yet having reached the reference zone (it being positioned downstream from the test zone). Timing is commenced when the signal attenuation of the test zone relative to the reference zone is greater than 10%. It should be mentioned that the value of 10% indicates the degree of confidence including any margin of error which has been attached to the measurement reading, which in itself depends on the various measurement parameters, e.g. test strip, optics. This might vary and be chosen to be any convenient value.

The liquid then proceeds into the reference zone and when the signal attenuation of the control zone relative to the reference zone is greater than minus 10% (−10%), the device considers that the liquid has reached the control zone (the minus value reflecting that the control zone is positioned downstream from the test zone). When the signal attenuation of the control zone relative to the reference zone is greater (i.e. more positive) than zero, the device determines that the liquid has reached the control zone. Thus the time measurement by the device may not necessarily exactly correspond to the time when the fluid arrives at the respective zones.

Although in this example the reader measures the rate of passage of liquid between the test and control zones, it measures it with respect to the signal obtained from the reference zone. However the arrival of liquid at the test and control zones could be determined absolutely, (i.e. not by measurement with respect to the reference zone).

The reader is also programmed to declare an assay result invalid if the liquid sample is detected at the control zone before it is detected at the reference zone, as this is indicative that the liquid sample has followed an abnormal flow path.

Example 16

A single set of optics is used to determine both the signal and the flow rate. The maximum and minimum flow rates are set at 5 and 40 s, respectively. Thus any sample that takes longer than 40 s is rejected as being too slow (which may be due to undersampling), any sample that is quicker than 5 s is rejected as being too fast. The flow rate will be influenced by a number of factors including porosity, distance between control and test-lines as well as any chemistry in the porous strip which might modify flow.

Timing is determined and set to zero when the fluid reaches the test-line. The timer is then set and the time for the fluid to reach the control line is measured. As a further control check, the device monitors that the fluid has passed through the reference zone. Additionally as a further control feature, the device also monitors that the fluid has passed through the test, reference and control zones in that order before it will accept a flow rate measurement as authentic, even if it satisfies the flow rate range of between 5 and 40 s.

In other embodiments, of course, the upper and lower flow rate limits can be set to a wide variety of values, in accordance with particular properties of test fluids and/or with the factors described above.

Example 17

An assay result reader according to the present disclosure may also include a system for declaring the result of an assay before completion of the assay, if a analyte measurement signal is above an upper threshold or below a lower threshold. Such systems are described in U.S. patent application Ser. No. 10/741,416, filed Dec. 19, 2003.

Example 18

An assay result reader according to the present disclosure may also include optical arrangement such as those described in U.S. Patent Application Ser. No. 60/508,001, filed Oct. 2, 2003.

All patents and patent applications referred to in this disclosure are hereby incorporated herein in their entireties by this reference.

We claim:

1. A device for determining an assay result, comprising:
a test strip comprising at least a first zone and a second zone spaced apart from one another along a flow path defined by the test strip;
a light source system configured to illuminate the first zone and the second zone of the test strip;
a light detection system configured to:
(a) detect light from the first zone of the test strip when the first zone is illuminated by the light source and output a first signal indicative of light detected from the first zone;
(b) detect light from the second zone of the test strip when the second zone is illuminated by the light source and output a second signal indicative of light detected from the second zone; and
(c) detect light from at least one of the zones when the respective zone is illuminated by the light source and output a third signal indicative of an amount of an analyte in that zone; and
a processor configured to:
(a) receive the first and second signals and, based at least in part on the first and second signals, determine a result indicative of a time required for a liquid received by the sample receiving zone to flow from the first zone along the flow path to the second zone; and
(b) receive the third signal, compare the third signal to a first threshold, compare the third signal to a second threshold, the second threshold being less than the first threshold, and generate an output signal if the third signal exceeds the first threshold or the third signal is less than the second threshold, the output signal indicative of a first result if the third signal exceeds the first threshold, or, alternatively, the output signal indicative of a second result if the third signal is less than the second threshold.

* * * * *